(12) United States Patent
Rurack et al.

(10) Patent No.: US 12,173,211 B2
(45) Date of Patent: Dec. 24, 2024

(54) FLUORESCENT PARTICLES WITH MOLECULARLY IMPRINTED FLUORESCENT POLYMER SHELLS FOR CELL STAINING APPLICATIONS IN CYTOMETRY AND MICROSCOPY

(71) Applicant: Bundesrepublik Deutschland, vertreten durch den Bundesminister für Wirtschaft und Energie, Berlin (DE)

(72) Inventors: Knut Rurack, Berlin (DE); Kornelia Gawlitza, Berlin (DE); Martha Wamaitha Kimani, Berlin (DE); Shan Jiang, Berlin (DE); Anette Gjörloff-Wingren, Malmö (SE); Zahra El-Schich, Malmö (SE); Yuecheng Zhang, Malmö (SE)

(73) Assignee: Bundesrepublik Deutschland, vertreten durch den Bundesminister für Wirtschaft und Energie, Berlin (DE)

( * ) Notice: Subject to any disclaimer, the term of this patent is extended or adjusted under 35 U.S.C. 154(b) by 921 days.

(21) Appl. No.: 17/254,474

(22) PCT Filed: Jun. 21, 2019

(86) PCT No.: PCT/EP2019/066550
§ 371 (c)(1),
(2) Date: Dec. 21, 2020

(87) PCT Pub. No.: WO2019/243617
PCT Pub. Date: Dec. 26, 2019

(65) Prior Publication Data
US 2021/0115328 A1     Apr. 22, 2021

(30) Foreign Application Priority Data
Jun. 22, 2018   (DE) ............... 10 2018 115 136.5

(51) Int. Cl.
*C09K 11/06*     (2006.01)
*B82Y 30/00*     (2011.01)
(Continued)

(52) U.S. Cl.
CPC .............. *C09K 11/06* (2013.01); *C09K 11/02* (2013.01); *C09K 11/616* (2013.01); *C09K 11/65* (2013.01);
(Continued)

(58) Field of Classification Search
CPC .............. C09K 11/06; C09K 11/77492; C09K 11/77062; C09K 11/77342; C09K 11/02;
(Continued)

(56) References Cited

FOREIGN PATENT DOCUMENTS

| CN | 103965504 A | 8/2014 |
|---|---|---|
| CN | 104327271 A | 2/2015 |

(Continued)

OTHER PUBLICATIONS

Amjadi el al . . . "A molecularly imprinted dual-emission carbon dot-quantum dot mesoporous hybrid for ratiometric determination of anti-inflammatory drug celecoxib", Spectrochimica Acta Part A: Molecular and Biomolecular Spectroscopy, vol. 191. pp. 345-351. (Oct. 10, 2017).*

(Continued)

*Primary Examiner* — C Melissa Koslow
(74) *Attorney, Agent, or Firm* — Bachman & LaPointe, P.C.

(57) ABSTRACT

A double fluorescent particle comprises: a core with a first fluorescence; and a molecularly imprinted polymer (MIP) shell with a second fluorescence; wherein the MIP is an organic polymer comprising elements selected from the group consisting of: C, H, O, N, P, and S; wherein the MIP is adapted to selectively bind to a cell surface structure; wherein the first fluorescence is generated by an entity (Continued)

selected from the group consisting of: a carbon nanodot, an alkaline earth metal fluoride, a dye-doped polymer, a dye-doped stabilized micelle, a P-dot—i.e. a π-conjugated polymer, a quantum dot doped polymer, a rare earth metal ion doped polymer, a dye-doped silica, a rare-earth ion doped silica, and a rare earth ion doped alkaline earth metal fluoride nanoparticle; wherein the second fluorescence is generated by an entity selected from the group consisting of: a dye, a molecular probe, an indicator, a probe monomer, an indicator monomer, and a cross-linker, and wherein the first and second fluorescence differ at least by an emission wavelength and/or by an excitation wavelength.

15 Claims, 25 Drawing Sheets

(51) Int. Cl.
| | |
|---|---|
| B82Y 35/00 | (2011.01) |
| B82Y 40/00 | (2011.01) |
| C09K 11/02 | (2006.01) |
| C09K 11/61 | (2006.01) |
| C09K 11/65 | (2006.01) |
| C09K 11/77 | (2006.01) |
| G01N 21/64 | (2006.01) |
| G01N 33/50 | (2006.01) |
| G01N 33/574 | (2006.01) |
| G01N 33/58 | (2006.01) |

(52) U.S. Cl.
CPC .. *C09K 11/77062* (2021.01); *C09K 11/77342* (2021.01); *C09K 11/77492* (2021.01); *C09K 11/7764* (2013.01); *G01N 21/64* (2013.01); *G01N 33/5005* (2013.01); *G01N 33/574* (2013.01); *G01N 33/582* (2013.01); *G01N 33/587* (2013.01); *B82Y 30/00* (2013.01); *B82Y 35/00* (2013.01); *B82Y 40/00* (2013.01); *C01P 2004/90* (2013.01); *C09K 2211/1416* (2013.01); *C09K 2211/145* (2013.01); *C09K 2211/1483* (2013.01); *G01N 2021/6419* (2013.01); *G01N 2021/6421* (2013.01); *G01N 2600/00* (2013.01)

(58) Field of Classification Search
CPC ..... C09K 11/616; C09K 11/65; C09K 11/774; C09K 2211/1483; C09K 2211/1416; C09K 2211/145; C01P 2004/90; B82Y 30/00; B82Y 35/00; B82Y 40/00
See application file for complete search history.

(56) References Cited

FOREIGN PATENT DOCUMENTS

| | | |
|---|---|---|
| EP | 1903075 A1 | 3/2008 |
| WO | 2018044688 A1 | 3/2018 |

OTHER PUBLICATIONS

Amjadi et al . . . "Molecularty imprinted mesoporous silica embedded with carbon dots and semiconductor quantum dots as a ratiometric fluorescent sensor For diniconazole". Biosensors and Bioelectronics. Elsevier Science Ltd. UK. Amsterdam. NL. vol. 96. Apr. 28, 2017 (Apr. 28, 2017). pp. 121-126.*

Database WPI Week 201524, Thomson Scientific, London, GB; AN 2015-20249V XP002794703, & CN 104 327 271 A (Univ Southwest) Feb. 4, 2015 (Feb. 4, 2015).

Database WPI Week 201469 Thomson Scientific, London, GB; AN 2014-T21787 XP002794704, & CN 103 965 504 A (Jiangsu United Chem Co Ltd) Aug. 6, 2014 (Aug. 6, 2014).

Amjadi et al., "A molecularly imprinted dual-emission carbon dot-quantum dot mesoporous hybrid for ratiometric determination of anti-inflammatory drug celecoxib", Spectrochimica Acta. Part A: Molecular and Biomolecular Spectroscopy, vol. 191, pp. 345-351, (Oct. 10, 2017).

Amjadi et al., "Molecularly imprinted mesoporous silica embedded with carbon dots and semiconductor quantum dots as a ratiometric fluorescent sensor for diniconazole", Biosensors and Bioelectronics, Elsevier Science Ltd. UK, Amsterdam, NL, vol. 96, Apr. 28, 2017 (Aug. 28, 2017), pp. 121-126.

Mao et al., "Efficient one-pot synthesis of molecularly imprinted silica nanospheres embedded carbon dots for fluorescent dopamine optosensing", Biosensors and Bioelectronics, Elsevier Science Ltd. UK, Amsterdam, NL, vol. 38, No. 1, (Apr. 29, 2012), pp. 55-60.

Ag et al., "Biofunctional quantum dots as fluorescence probe for cell-specifictargeting", Colloids and Surfaces B: Biointerfaces, vol. 114 (2014) pp. 96-103.

Demir et al., "Tracking Hyaluronan: Molecularly Imprinted Polymer Coated Carbon Dots for Cancer Cell Targeting and Imaging", ACS Applied Materials & Interfaces (2018), vol. 10, pp. 3305-3313.

Holzapfel et al., "Preparation of Fluorescent Carboxyl and Amino Functionalized Polystyrene Particles by Miniemulsion Polymerization as Markers for Cells", Macromolecular Chemistry and Physics, (2005), vol. 206, 2440-2449.

Long et al., "Multiplex immunodetection of tumor markers with a suspension array built upon core-shell structured functional fluorescence-encoded microspheres", Analytica Chimica Acta, vol. 665 (2010), pp. 63-68.

Stsiapura et al., "Functionalized nanocrystal-tagged fluorescent polymer beads: synthesis, physicochemical characterization, and immunolabeling application", Analytical Biochemistry, vol. 334, (2004), pp. 257-265.

International search report for patent application No. PCT/EP2019/066550 dated Oct. 1, 2019.

Jones, E.R., Semsarilar, M., Blanazs, A., and Armes, S.P. (2012). Efficient Synthesis of Amine-Functional Diblock Copolymer Nanoparticles via RAFT Dispersion Polymerization of Benzyl Methacrylate in Alcoholic Media. Macromolecules 45: 5091-5098.

Ritter, B., Haida, P., Fink, F., Krahl, T., Gawlitza, K., Rurack, K., Scholz, G., Kemnitz, E. (2017). Novel and easy access to highly luminescent Eu and Tb doped ultra-small CaF2, SrF2 and BaF2 nanoparticles—structure and luminescence. Dalton Transactions 46: 2925-2936.

* cited by examiner

FLUORESCENT PARTICLES WITH MOLECULARLY IMPRINTED FLUORESCENT POLYMER SHELLS FOR CELL STAINING APPLICATIONS IN CYTOMETRY AND MICROSCOPY

FIELD AND BACKGROUND

The present invention relates to fluorescence based detection methods in cell biology and medical diagnostics for the rapid and sensitive detection of certain primary cells and cell lines, e.g. cancer cells. In particular, the present invention relates to fluorescence targeting and detection of biomarkers on live and fixated cells using molecularly imprinted polymers (MIPs).

Known MIP-based sensors in imaging and analysis almost exclusively refer to single-signal systems. Especially in complex samples, single-signal measurements are often affected by changes in concentration or an inhomogeneous distribution of the sensors, instrumental fluctuations, and environmental conditions, which hamper quantitative determination. Compared with single-signal output, ratiometric or dual-signal recording is independent of sensor and reagent concentration and provides an intrinsic correction to overcome potential effects from the instrument and the background and therefore, allow unequivocal identification of sought for cells.

Current well-established techniques utilize magnetic resonance imaging (MRI) and computed tomography (CT scans) for in vivo imaging of groups of (cancer) cells. For in vitro imaging of single cells, flow cytometry and histochemical techniques are usually employed, where cells are tagged or stained with fluorescent dyes. Current microscopy techniques use fluorescent polymer beads carrying specific antibodies for cell surface staining (Stsiapura et al., 2004), or fluorescent polymer cores carrying functional groups that permit uptake by tumor cells (Holzapfel et al., 2005). The fluorescent polymer cores may contain dyes or quantum dots as fluorescent units (Stsiapura et al., 2004). Quantum dots tagged with antibodies targeting cell surfaces have also been used (Ag et al., 2014). Current cytometry uses fluorescently labeled antibodies and lectins for the staining of cell surface entities and the subsequent isolation of the labeled cells (Long et al., 2010). Molecularly imprinted silica nanospheres with embedded carbon nanodots (CNDs) were used in a dopamine fluorescence optosensor (Mao et al., 2012). CNDs coupled with non-fluorescent MIP layers were employed as a biocompatible optical imaging tool for probing cancer biomarkers (Demir et al., 2018). These two systems are based on a fluorescent CND core with a non-fluorescent MIP shell and are still single-signal sensing methods. A CND-doped silica core with a quantum dot-(QD) doped molecularly imprinted silica shell (MIS) has been used for fungicide detection in agricultural analyses (Amjadi and Jalili, 2017) and for the detection of an anti-inflammatory drug (Amjadi and Jalili, 2018).

BRIEF SUMMARY

Against this background, according to an embodiment a double fluorescent particle is suggested, the particle comprising: a core having a first fluorescence; and a molecularly imprinted polymer (MIP) shell having a second fluorescence, wherein the molecularly imprinted polymer is an organic polymer comprising elements selected from the group consisting of: C, H, O, N, P, and S; wherein the MIP is adapted to selectively bind to a cell surface structure; wherein the first fluorescence is generated by an entity, selected from the group consisting of: a carbon nanodot, a dye-doped polymer, a dye-doped stabilized micelle, a P-dot (i.e. π-conjugated polymer), a quantum dot doped polymer, a rare earth metal ion doped polymer, a dye-doped silica, a rare-earth ion doped silica, and a rare earth ion doped alkaline earth metal fluoride nanoparticle; wherein the second fluorescence is generated by an entity selected from the group consisting of: a dye, a molecular probe, an indicator, a probe monomer, and an indicator monomer; wherein the first and second fluorescence differ at least by an emission wavelength and/or by an excitation wavelength.

Further, a method of screening for a target cell in a sample is provided, the target cell being characterized by a specific cell surface structure, i.e. by a specific membrane marker structure. The suggested method comprises: providing a double fluorescent particle as described above and further below; allowing a contact between the double fluorescent particle and a plurality of cells from the sample, potentially comprising a cell having the specific cell surface structure; detecting a cell having the specific cell surface structure with bound thereto double fluorescing particles; and determining a presence of the target cell in the sample.

Further, a method for establishing a target cell line is suggested, wherein the cells of the cell line are characterized by a specific cell surface structure, i.e. a membrane marker structure, the method comprising isolating from a multitude of cells the target cell specified by the screening method as described above and further below.

Further, a use of a double fluorescent particle as described above and further below is suggested for in vitro identification and/or characterization of circulating tumor cells in a blood sample.

Further, a use of a double fluorescent particle as described above and further below is suggested for identifying a cell, a cell line, or a hybridoma, wherein the cell, the cell line and the hybridoma produces a specific immunoglobulin or a specific cytokine.

Further, an imaging technique for cancer detection in a tissue is suggested, wherein the imaging technique comprises detecting a fluorescence ratio at a double fluorescent particle and generating an image of the tissue, wherein cells of the tissue with a surface structure recognized by at least one double fluorescing particle as described above are highlighted against a background of the image.

Furthermore, a cell sorting technique is suggested, the technique comprising: labelling a cell with the double fluorescent particle suggested above, detecting a ratio of first and second fluorescence signals; and registering the presence of a cell which is labelled by the double fluorescent particle.

BRIEF DESCRIPTION OF THE DRAWINGS

A full and enabling disclosure of the present invention, including the best mode thereof, to one of ordinary skill in the art, is set forth more particularly in the remainder of the description, including reference to the accompanying figures.

Figure 1:
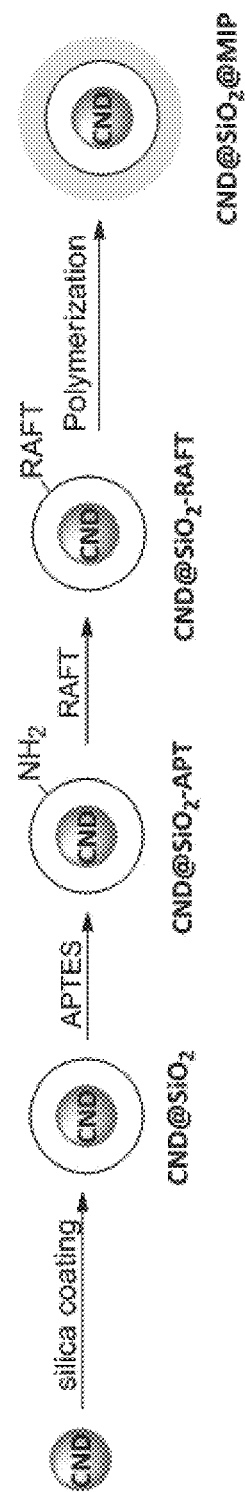
FIG. 1 shows schematically the generation of a double fluorescent particle according to example 1, i.e. the synthetic path to and architecture of CND@SiO$_2$@MIP.

In the following detailed description, reference is made to the accompanying figures, which form a part hereof, and in which show by way of illustration specific embodiments and features of the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

DETAILED DESCRIPTION

As used in this description (above and below) and claims, the use of the word "a" or "an" when used in conjunction with the term "comprising" in the claims and/or the specification may mean "one", but it is also consistent with the meaning of "one or more", "at least one", and "one or more than one".

As used in this description (above and below) and claims, the use of the word "or" in the claims is used to mean "and/or" unless explicitly indicated to refer to alternatives only or the alternatives are mutually exclusive, although the disclosure supports a definition that refers to only alternatives and "and/or".

As used in this description (above and below) and claims, the used word "about" before a numerical value indicates a range of numerical values encompassing, i.e. including, a statistical deviation from the indicated numerical value by ±5%.

As used in this description (above and below) and claims, the words "comprising" (and any form of comprising, such as "comprise" and "comprises"), "having" (and any form of having, such as "have" and "has"), "including" (and any form of including, such as "includes" and "include"), "containing" (and any form of containing, such as "contains" and "contain") or "encompassing" (and any form of encompassing, such as "encompass" and "encompasses") are inclusive or open-ended and do not exclude additional, unrecited elements or method steps.

As used in this description (above and below) and claims, the term "nanoparticle" is to be understood as encompassing typically a solid body having an arithmetically mean diameter of between 1 nm and 1000 nm. Typically, the nanoparticles as used in the present description and claims either as CND or ready core/shell particles comprising a core and a MIP shell (or possibly a structural inorganic layer in between the core and the MIP shell), comprise particles with a mean diameter≤200 nm. Preferably, cores start with a diameter of 5 nm, see CNDs, and should typically go up to 100 nm, yet also cores up to 200 nm can be used. A well-established method to measure the diameter of such solid bodies is, e.g., electron microscopy, especially scanning electron microscopy or transmission electron microscopy. Other methods comprise, e.g., light scattering, especially dynamic light scattering. However, the latter methods require defining the refractive index of the related solid material which may be difficult to indicate for particles below 50 nm, whereby the problem is even more pronounced for composites/hybrids such as dye-doped PS, silica-shelled organic particles or CNDs, etc. Therefore, as used therein, the indicated particle size relates to values as detected by electron microscopy using the signals generated in transmission electron microscopy (TEM) or in scanning electron microscopy. For electron microscopy the signal generated by backscattered electrons as measured with, e.g., a BSE detector of a commercially available electron microscope can be used to establish the particle diameter and to calculate a corresponding mean value. For transmission electron microscopy a FEI Talos™ F200S (200 kV) scanning/transmission electron microscope was used.

Usually, the term "molecularly imprinted polymer" (MIP) relates to polymer networks comprising quasi inorganic building blocks and/or organic building blocks consisting of the elements carbon, oxygen, hydrogen, and possibly nitrogen, phosphorus, and sulphur, which have been generated in the presence of a special template. Purely inorganic MIPs do not really exist, except for the very first examples of ca. 100 years ago (which yet had not been termed "MIP" then), in which only TEOS was used so that the resulting polymer was only a $SiO_2$ polymer. Imprinted silicas today are "quasi-inorganic" MIPs because, at least up to now, always various organically modified silanes were used as monomer and crosslinker units.

For the sake of clarity, in the present description and claims molecularly imprinted silicas will be referred to as MISs instead of MIPs. Against this background MIPs as used in this description, drawings, and claims will be understood to comprise only organic polymers which typically are prepared without any functional silanes. Generally, MIPs are highly cross-linked polymers which are prepared from monomers and cross-linkers in the presence of a target molecule as template. Organic polymers consist typically of chemical elements selected from C, H, O, N, S, and P. After removal of the template molecule, a specific, three-dimensional recognition site or 'pocket' that is complementary in size, shape, and specific interaction signature to the template molecule is retained in the polymer matrix. MIPs thus can combine strong affinity to the template molecule with high selectivity, mimicking natural receptors such as antibodies or substrate recognition sites of enzymes. However, especially the chemical and thermal stabilities make MIPs and MISs more suitable for many applications than their natural analogues. In addition, starting materials for MIPs and MISs are often abundant and considerably cheap and preparation times are on the order of days rather than weeks or months typically required for obtaining high-performance biological receptors. Various methods including radical polymerization, metathesis, and living polymerization such as reversible addition-fragmentation chain transfer (RAFT) and metal-catalyzed atom transfer radical polymerization (ATRP) have been adopted for MIP preparation.

In general, the MIP-polymer will grow starting at the surface of the core (see, cf. Item 1.6 to 1.8 and 2.6 to 2.8, 3.4-3.6, and 4.4-4.6 in the experimental section). Usually, amino groups are fixed on the surface of the core and a so-called RAFT-agent, which allows grafting a polymer from a surface.

As used in this description (above and below) and claims, the terms "fluorescence", "fluorescent", "fluorescence measurement", "fluorescent dye", "fluorescent particle", "fluorescent ion", "fluorescent monomer", "fluorescent probe monomer", "fluorescent indicator monomer", "fluorescent cross-linker", "fluorescent probe cross-linker", "fluorescent indicator cross-linker" and any related thereto term is to be understood as comprising an optical property or its detection, e.g., an excitation wavelength, an emission wavelength, a fluorescence intensity, a fluorescence quantum yield, a fluorescence lifetime or decay, a fluorescence quenching or bleaching and/or a ratio of any of their values and its(their) detection. Put differently, a fluorescence and a luminescence comprise an excitation and an emission as well as an excitation wavelength (and/or wavelength range) and an emission wavelength (and/or wavelength range).

In particular, a fluorescence of an entity, e.g. a chemical substance or ion, is typically characterized by an excitation wavelength (to be precise, typically an excitation wavelength range) and an emission wavelength (to be precise, typically an emission wavelength range). Typically, each of the indicated ranges has a distinct maximum. Accordingly, a "first fluorescence" as used herein comprises a "first excitation wavelength" and a "first excitation wavelength range" and a "first emission wavelength" and a "first emission wavelength range". Fluorescence ratio measurements or ratiometric fluorescence measurements are measurements of two fluorescences of two fluorescent species, one of which is commonly immune against the analyte and the other is changing as a function of the presence of the analyte, whereby both fluorescences can be excited in the same excitation wavelength range or in two different excitation wavelength ranges. Their fluorescence emission ranges have to be at least so much different that the decrease/increase of the analyte-susceptible band can be distinguished from the emission of the constant band. Ratiometric measurements have the advantages that fluctuations of the light source's intensity, photodegradation or environmental changes can be accounted for. Such internal referencing makes the analysis of the analyte-dependent signal much more reliable.

Fluorescent entities are selected from carbon nanodots (CND), quantum dots (QD) such as CdTe, CdSe, CdSe/ZnS, and Mn-doped ZnS, fluorescent dyes such as listed under class 2 of the table below, indicator dyes such as listed in classes #1, #2, and #3 in the table below, fluorescent molecular probes such as indicated in classes #1, #2, and #3 of this table as well as, rare earth metal ions such as cerium (Ce), europium (Eu), gadolinium (Gd), neodymium (Nd), scandium (Sc), terbium (Tb), ytterbium (Yb), yttrium (Y), dysprosium (Dy), samarium (Sm), holmium (Ho), erbium (Er), thulium (Tm), and praseodymium (Pr), and substances as indicated in class #2 of the table below.

TABLE 1

Classes of fluorescent entities.

| Class | Fluorescent entities |
|---|---|
| #1 | Rhodamine and derivatives |
| | Fluorescein and derivatives |
| | Styryl derivatives |
| | Cyanine and polymethine derivatives |
| | Pyridinium derivatives |
| | Pyrylium and thiopyrylium derivatives |
| | Ruthenium, osmium or iridium complexes and derivatives |
| | Luminescent complexes of rare earth elements (such as europium or terbium) |
| | Squarylium and derivatives |
| #2 | Coumarin and derivatives |
| | Dipyrromethene or BODIPY and derivatives |
| | Pyrromethane and derivatives |
| | Benzofuran and derivatives |
| | Pyridine derivatives |
| | Naphthalimide and derivatives |
| | Benzoxazole and derivatives |
| | Benzoxadiazole and derivatives |
| | Benzindole and derivatives |
| | DAPI and derivatives |
| | Stilbene and derivatives |
| | Oxazine and derivatives |
| | Perylene and derivatives |

TABLE 1-continued

Classes of fluorescent entities.

| Class | Fluorescent entities |
|---|---|
| | Azulene and derivatives |
| | Styryl base derivatives |
| | Phycoerythrin and derivatives |
| | Squaraine and derivatives |
| | Porphyrine and derivatives |
| | Phthalocyanine and derivatives |
| | Phenazines and their derivatives |
| | Diphenylacetylene and its derivatives |
| #3 | Cationic and anionic derivatives of all the dyes in #2. |

For the sake of clarity, as the luminescence properties, e.g. of a dye, a quantum dot, a rare earth metal ion, and a rare earth ion may be changed upon their covalent linkage to a monomer, to a polymer, to a silane, to a silica, to a fluoride nanoparticle or a micelle, entities such as dye-doped polymers, dye-doped stabilized micelles, a P-dot (a π-conjugated polymer), quantum dot doped polymers, rare earth metal ion doped polymers, dye doped silica, and rare earth ion doped alkaline earth metal fluoride nanoparticles are referred to as fluorescent entities as well. Therein the terms "rare earth metal ion" and "rare earth ion" and "rare earth metal" are considered to be synonymous.

As to the first fluorescence which characterizes the core, different fluorophores can be used in order to produce it. Carbon nanodots advantageously offer a size-dependent photoluminescence emission, strong luminescence, and high resistance to photobleaching. They have advantages over semiconductor quantum dots, such as low cost, high chemical and photostability, and biocompatibility.

CNDs can be classified as follows: blue CNDs: emission: 440 nm (excitation at 365 nm) size: about 5 nm; green CNDs: emission: 518 nm (excitation at 365 nm) size: about 5 nm; yellow CNDs: emission: 547 nm (excitation at 470 nm) size: about 6 nm; red CNDs: emission: 610 nm (excitation at 520 nm) size: about 5 nm; red CNDs: emission: 720 nm (excitation at 580 nm) size: 5 nm. CNDs for the described application can be selected from all these either as pure batches or in combination with each other.

The luminescence of dye-doped polymers, dye-doped silica and dye-doped stabilized micelles depends largely on the dye involved. Its fluorescence can be both enhanced and stabilized if the dye is enclosed in a shell, e.g. entrapped in micelles or in particles. With respect to the quantum dot doped polymers, rare earth metal ion doped polymers, a rare-earth ion doped silica, and rare earth ion doped alkaline earth metal fluoride nanoparticles we note, that the respective fluorophores can be selected such as to provide a reliable discrimination between first and second fluorescence signals. Herein, the excitation wavelength/range is not as important as emission wavelength(s)/range(s). Typically, both emissions, i.e. the emission signal from the first fluorescence (core) and the emission signal from the second fluorescence (MIP shell) can be excited with the same light source; in the strict sense of the ratiometric measurement this would be even the ideal case. However, this is difficult to accomplish in reality because of the different properties of fluorescent materials. Regarding discrimination of the two emissions, this depends on the type of emission (e.g. line shapes of rare earth ions vs. broader bands of organic dyes) and the wavelength resolving power of the detection setup. Cytometers often operate with rather narrow band pass filters of 20-30 nm so that such a difference in maxima shall be sufficient, if the half-width of the band is <twice this value and the two intensities are not too different. As a rule of thumb: the more different the two intensities of core and shell are, the better separated the bands shall be, so that a weak band can still be detected with reasonable uncertainty besides an intense one.

Rare-earth metal ion-doped silica or alkaline-earth metal fluoride particles, in particular when using $Eu^{3+}$ and $Tb^{3+}$ for doping, possess the advantage that they can be excited at in a broad spectral window from the UV up to 450 nm and yield an emission that consists of multiple narrow lines and can thus be easily discriminated against overlapping broad emission bands of dyes.

As to the second fluorescence, by which the MIP shell is characterized, it may typically be generated by an indicator or a probe molecule which is incorporated into the MIP. As to the incorporation, a mere physical entrapment or adsorption vs. a covalent linkage is possible. The terms "probe" and "indicator" are often used synonymously. "Molecular probe" (or "molecular indicator") means that the probe/indicator molecules are only sterically integrated (entrapped) into the polymer matrix of the molecularly imprinted polymer. The terms "probe monomer" as well as "indicator monomer", however, mean that these molecules carry a reactive anchor that allows their covalent incorporation into the polymer matrix by polymerization. Of course, this is usually the more stable and preferred variant, but there are also indicators (probes) where the synthetic effort for generating such a reactive derivative (of the indicator/probe) is too high and the path of steric incorporation into the polymer matrix is easier accessible. As already mentioned above, these can also be "fluorescent probe or fluorescent indicator cross-linkers".

The technical object of the described embodiments is to provide an agent and a method for staining, i.e. fluorescent labeling, of live cells. Therein, of particular interest are glycosylated proteins and glycosylated lipids known as tumor markers on cancer cells whose presence shall be optically detectable, e.g. by a fluorescence signal in microscopy and/or flow cytometry. For the indicated purpose, fluorescent core-fluorescent MIP shell particles as described above and below are suggested. These particles have typically diameters below 50 nm, particularly diameters between 20 and 40 nm. The thickness of the silica shell is typically about 20 nm and can be tuned by changing the hydrolysis conditions. The thickness of the MIP shell is about 10 nm, and can be tuned by changing the amounts of monomers, cross-linkers and polymerization conditions. Typically, the MIP shell surrounding the fluorescent core has a thickness of about 10 nm. The shell thickness can be tuned. However, a shell thickness above 10 nm is problematic: on one hand, the entity to be recognized is bound to a cell surface, i.e., cannot diffuse into the polymer matrix. On the other hand, a thick shell has homogeneously distributed fluorescent monomers, i.e. generates a fluorescence signal over the entire thickness. The more of the fluorescent monomers are lying in a region into which the cell surface residues cannot each, the higher the background signal. Of course, this always depends on the imprinting process, but at present, MIPs are generated using soluble low molecular weight templates such as SA. So far a kind of epitope imprinting was used which generates cavities throughout the whole MIP shell. Because only the outermost layer will bind to the cell surface, shell thicknesses preferably are kept thin, at best ca.≤10 nm. However, MIPs can also be generated by imprinting at the cell surface, e.g. at formalin-fixated cell surfaces, like it would be for true artificial antibodies.

According to an embodiment a double fluorescent particle is suggested, wherein the double fluorescing particle comprises:
- a core, having a first fluorescence; and
- a molecularly imprinted polymer (MIP) shell having a second fluorescence,
- wherein the molecularly imprinted polymer is an organic polymer comprising elements selected from the group consisting of: C, H, O, N, P, and S; and wherein the MIP is adapted to selectively bind to a cell surface structure;

wherein the first fluorescence is generated by an entity, selected from the group consisting of: a carbon nanodot, a dye-doped polymer, a dye-doped stabilized micelle, a P-dot (a π-conjugated polymer), a quantum dot doped polymer, a rare earth metal ion doped polymer, a dye-doped silica, a rare-earth ion doped silica, and a rare earth ion doped alkaline earth metal fluoride nanoparticle;
- wherein the second fluorescence is generated by an entity selected from the group consisting of: a dye, a molecular probe, an indicator, a probe monomer, an indicator monomer, and a cross-linker; and
- wherein the first and second fluorescence differ at least by an emission wavelength and/or by an excitation wavelength.

Herein, the terms "first fluorescence" and "second fluorescence" include or are equivalent to the terms "first fluorescence signal" and "first luminescence signal" and "second fluorescence signal" and "second luminescence signal", respectively. As explained in more detail further below, "fluorescence" and "luminescence" of an entity comprise the emission of a light whose intensity can be measured. Measured values can be used to calculate a ratio or, after suitable calibration, to calculate a concentration of a dye (particle) emitting the signal, or simply to visualize a certain object, labelled by the particle. Advantageously, using a ratio of the first fluorescence and the second fluorescence the reliability of a measurement signal can significantly be improved as the ratio does not depend, e.g., on an intensity of the excitation light. Typical measurement set-ups comprise laser/laser diode excitation sources in microscopes and cytometers. If different lines of a single laser can be chosen, the problem does not occur. If two different lasers have to be used, their behavior/drift can be different, though they are usually rather similarly stable and stabilized and are operated through the same control unit. Therefore, the lasers are not the problems here, but rather the focus: If particles migrate in the laser focus, whether in a sample under the microscope or in the cytometer measurement channel, intensity changes will result which are not due to a change in concentration but simply due to defocusing. However, these can be easily corrected for with a core's constant fluorescence. The micelles may favorably be generated as described, e.g., by Jones et al. (2012). Rare earth ions, which may be associated with organic ligands, may simply be included into the polymer matrix by diffusion, similarly to the dyes II as described below. The polymer shell which comprises the molecularly imprinted polymer allows the double fluorescent particle to be bound at a cell surface structure corresponding to the specificity of the molecularly imprinted polymer. Certain cell(s) thus can be selectively labelled and be recognized or counted, i.e. in a cell sorting device.

According to an embodiment, the core of the suggested double fluorescent particle comprises: an inorganic material selected from a carbon dot and a silica nanoparticle and an alkaline earth metal fluoride or an organic material selected from a polystyrene and a π-conjugated polymer.

According to a modification of the embodiment above, the core comprises a π-conjugated polymer selected from: a polyfluorene, e.g. poly(9,9-di-n-hexyl-fluorene-2,7-diyl or poly[9,9-di-(2'-ethylhexyl) fluorenyl-2,7-diyl] (PDHF), and poly(9,9-dioctylfluorene) (PFO); a poly(phenylene ethynylene), e.g. PPE; a poly(phenylene vinylene), e.g. poly(2-methoxy-5-(2'-ethyl) hexoxy-phenylenevinylene) (MEH-PPV), poly[2-methoxy-5-(3',7'-dimethyloctyloxy)-1,4-phenylene vinylene] (MDMO-PPV), or a cyano-substituted poly(p-phenylene vinylene) (CN-PPV); a fluorene-based copolymer, e.g. poly[{9,9-dioctyl-2,7-divinylenefluorenylene}-alt-co-{2-methoxy-5-(2-ethylhexyloxy)-1,4-phenylene}] (PFPV); a poly[9,9-dioctylfluorenyl-2,7-diyl)-co-1,4-benzo-{2,1'-3}-thiadiazole)] (PFBT); a polyfluorenyl-dithienylbenzothiadiazole (PF-DBT5); and a derivative thereof.

In other words, the cores can comprise mainly an organic material, especially a polymer such as polystyrene or a P-dot or (alternatively) an inorganic material, especially a carbon dot or a silica nanoparticle. P-dots are a type of nanoparticles, which primarily consist of π-conjugated (i.e. semi-conducting) polymers, have relatively small particle size (20-200 nm) and exhibit a bright fluorescence. Corresponding luminophores directly applicable as core can be selected from, e.g.: polyfluorene—such as poly(9,9-di-n-hexyl-fluorene-2,7-diyl or poly[9,9-di-(2'-ethylhexyl) fluorenyl-2,7-diyl] (PDHF) and poly(9,9-dioctylfluorene) (PFO); poly (phenylene ethynylene)—such as PPE; poly(phenylene vinylene)—such as poly(2-methoxy-5-(2'-ethyl)-hexoxy-phenylenevinylene) (MEH-PPV), poly[2-methoxy-5-(3',7'-dimethyloctyloxy)-1,4-phenylene vinylene] (MDMO-PPV) and cyano-substituted poly(p-phenylene vinylene) (CN-PPV); fluorene-based copolymers—such as poly[{9,9-dioctyl-2,7-divinylenefluorenylene}-alt-co-{2-methoxy-5-(2-ethylhexyloxy)-1,4-phenylene}] (PFPV); poly[9,9-dioctylfluorenyl-2,7-diyl)-co-1,4-benzo-{2,1'-3}-thiadiazole)](PFBT); and polyfluorenyl-dithienylbenzothiadiazole (PF-DBT5); and derivatives thereof.

Advantageously, such cores fluoresce by themselves and therefore, do not need to be labelled separately. Accordingly, the preparation of corresponding double fluorescent core/shell particles is simplified. The double fluorescent particles advantageously can be tuned according to the intended application and measurement conditions with respect to fluorescence, size, and analyte specificity.

According to an embodiment, the double fluorescent particle further comprises:
- a structural shell comprising $SiO_2$ or $TiO_2$ which covers the core,
- wherein the molecularly imprinted polymer shell is disposed atop the structural shell.

Advantageously, the inorganic shell allows to increase the surface of the core and to conveniently provide e.g. reactive groups carried by silanes such as APTES for anchoring the following MIP shell. For the inorganic emitters and CNDs, it provides a conjugation layer from which the MIPs can be grown. For doped polymer beads, it additionally shields the polymer core so that during the further synthetic attachment of reagents and MIP, the polymer core is not dissolved or the sterically embedded dye is leaching out. In a biological environment, it also shields the core from attack by small species that might alter the fluorescence of a core such as protons (many of the inorganic cores show a certain pH dependence of their fluorescence).

However, the structural shell which covers the core, the core comprising the first fluorescence, can be omitted if the core is a silica particle, comprising the first fluorescence. Typical silica particles which are used as cores of the suggested double-fluorescent core/shell particles are rather rough (cf. FIG. 24, top) and not as smooth as typical polymer cores (cf. FIG. 13). Therefore, the structural shell is not necessarily required for silica particle cores. As illustrated by TEM-images in FIG. 24, larger dye-doped silica particles are smoother, than smaller ones. Since cell uptake (endocytosis) behavior may vary depending on particle size, the selection of the core size allows for different applications, e.g. in imaging diagnostics. In particular, the potential cell uptake (endocytosis) behavior of nanoparticles differs for particles<<100 nm to those >100 nm. Thus, the suggested core synthesis allows for a wide range of applications.

According to an embodiment, a median arithmetic diameter of the double fluorescent particle as measured with an electron microscope lies in a range selected from 20 nm to less than 100 nm.

Advantageously, by adjusting the size of the particles their incorporation by cells can be controlled or even triggered.

According to an embodiment, a thickness of the molecularly imprinted polymer shell is selected from 2 nm to 25 nm, particularly from 5 nm to 15 nm, preferably from 5 nm to 10 nm.

Advantages arise for improved signal/noise ratio as discussed of controlling the thickness have been discussed above.

According to an embodiment, the molecularly imprinted polymer of the MIP shell binds a glycan selected from: N-acetylneuraminic acid (Neu5Ac, human form of sialic acid (SA)), N-glycolylneuraminic acid (Neu5Gc, animal form of sialic acid), Siaα2-6GalNAc (Sialyl Tn), Siaα2-3Galβ 1-3GalNAc (Sialyl T), Siaα 2,3 Galβ 1,4(Fucα 1,3) GlcNAc (Sialyl Lewis$^X$), or Sia2,3Galβ 1,3(Fucα 1,4) GlcNAc (Sialyl Lewis$^4$), Siaα2,3-Galβ, Siaα2,6-Galβ, Siaα2,3-N-acetyllactosamine, Siaα2,6-N-acetyllactosamine, GlcA2SO$_3$1,4-Glc2NSO$_3$ or GlcA2SO$_3$ 1,4-Glc2NSO$_3$6SO$_3$. Neu5Acα2-3Neu5Acα or eu5Acα2-6Neu5Acα. For instance, sialyl Tn is described Neu5Acα2-6GalNAcα1-, Sialyl T is described as Neu5Acα2-3Galβ1-3GalNAcα; Sialyl Lewis$^4$ is described as Neu5Acα2-3Galβ1-3[Fucα1-4]GlcNAcβ-, Sialyl Lewis$^X$ is described as Neu5Acα2-3Galβ1-4[Fucα1-3]GlcNAcβ-; Neu5Acα2-3Galβ, Neu5Acα2-6Galβ can be used as well for molecular imprinting.

Advantageously, these structures are present at the surface of different differentiation stages of immune competent cells or can be associated with a tumor cell.

According to an embodiment, a the molecularly imprinted polymer is generated by a polymerization of at least one type of a monomer selected from: acrylamide, vinyl pyridine, N-isopropylacrylamide, 2-hydroxyethyl methacrylate, methyl methacrylate, benzyl methacrylate, methacrylate, methacrylamide, N,N'-dimethyl methacrylamide, trifluoromethyl acrylate, 2-aminoethyl methacrylate, vinylalcohol, vinylimidazole, vinylphenyl boronic acid, amino-substituted vinylphenyl boronic acid, vinyl benzaldehyde, vinyl aniline; with a crosslinking agent selected from: ethylene dimethacrylate, ethylene glycol dimethacrylate, N,N'-methylenediacrylamide, divinylbenzene, tetramethylene dimethacrylate, poly(acrylic acid), a bis(-hydroxyethyl) sulfone, trimethylolpropane trimethacrylate, and pentaerythritol triacrylate.

Advantageously, these monomers and cross-linker molecules are water soluble or soluble in mixed aqueous solutions such as water/methanol mixtures or methanol and allow to be polymerized in presence of the relevant template molecules. Relevant template molecules typically comprise sugar acids, glycans and glycopeptides which are quite susceptible to the solvent conditions. Advantageously, in buffered aqueous solutions which can be used for polymerization of the indicated monomers and cross-linkers these sugar acids, glycans and glycopeptides maintain their native structure, i.e. can be prevented from denaturation.

According to an embodiment, the rare earth metal ion is selected from: cerium (Ce), europium (Eu), gadolinium (Gd), neodymium (Nd), scandium (Sc), terbium (Tb), ytterbium (Yb), and yttrium (Y), dysprodium (Dy), samarium (Sm), holmium (Ho), erbium (Er), thulium (Tm), and praseodymium (Pr).

Advantageously, these rare earth metal ions exhibit fluorescence properties which typically do not require unusual optical filter settings. In other words, standard laboratory equipment can be used to excite and measure respective luminescence.

According to an embodiment, the rare earth ion doped alkaline earth metal fluoride nanoparticle comprises a fluoride of Ca, Ba, or Sr; and the rare earth ion is selected from: Ce, Eu and Tb.

Advantageously, the rare earth ion doped alkaline earth metal fluoride nanoparticles as described, e.g., by Ritter et al. (2017), typically have of a size below 5 nm may carry on their surface hydrophobic ligands. They may be incorporated into the polymer core either sterically or as described below under item 2.4. These particles are easily accessible at room temperature and have a size of between 3 and 20 nm. Particles of such size can be easily incorporated into the polymer core. Advantageously, fine tuning of the luminescence properties can be accomplished by variation of the Ca-to-Sr ratio. Co-doping with Ce$^{3+}$ and Tb$^{3+}$ results in a huge increase (>50 times) of the green luminescence intensity due to energy transfer Ce$^{3+}$→Tb$^{3+}$.

Similarly thereto, according to an embodiment, the rare earth ion of the rare-earth ion doped silica is selected from: Terbium and Europium. Advantages are corresponding ones.

According to another embodiment a method of screening for a target cell in a sample is suggested, wherein the target cell is characterized by a cell surface structure, i.e. a membrane marker structure, and the method comprises:
  providing a double fluorescent particle as described in any of the embodiments above;
  allowing a contact between the double fluorescent particle and a plurality of cells from the sample, potentially comprising a cell having the cell surface structure (i.e. the membrane marker structure);
  detecting a cell having the cell surface structure (i.e. the membrane marker structure) with bound thereto double fluorescing particles;
  determining a presence of the target cell in the sample.

Advantageously, cell screening methods are a typical prerequisite for many practically important detection schemes. The detection of circulating tumor cells, the onset of metastasis can be detected via cell screening. Current methods to detect circulating tumor cells are not good enough and glycan markers are not explored due to low binding ligands. The double fluorescent particles will detect the tumor cell specific surface structures and complement current methods using antibodies or dyes against other biomarkers.

According to an embodiment, the above process "detecting of the cell" comprises measuring a ratio of a first fluorescence and a second fluorescence of the double fluorescent particle.

Advantageously, the detection of certain signal ratio is a common feature of any modern cell sorter apparatus (FACS-Scan). In particular, a ratio of fluorescence emission signals measured at different channels can be used for identifying a certain cell type. The double fluorescent particles will make a very sensitive signal after binding, which can be easily measured with flow cytometry.

According to an embodiment, the cell surface structure is a glycosylated protein or a glycosylated lipid.

Advantageously, the detection of glycoside structures and their comparison allows identifying alterations in glycosylation as biomarkers for cancer detection. For example, the detection of sialic acid glycoprotein and glycolipid structures in tumor tissues and normal controls can be used to verify a diagnosis or to evaluate the efficiency of an active substance or drug. With double fluorescent and very specific particles against sialic acid, the detection of tumor cells expressing high levels of sialic acid will be easily selected from normal cells, since those most of the time express very little of sialic acid.

According to an embodiment, the above method further comprises:

isolating the target cell.

Typically, modern biotechnology and animal cell culture is based on single cells. To isolate a target cell in order to establish a cell line the target cell at first must be identified. Such identification can be reached using the suggested method with great sensitivity. All cells expressing high levels of sialic acid could be captured and isolated with the help of highly specific fluorescent sialic acid-specific nanoparticles.

According to an embodiment a method for establishing a target cell line is suggested, wherein the cells of the target cell line are characterized by a cell surface structure, also known as a membrane marker structure. Typically the cell surface structure comprises a glycosylated protein and/or a glycosylated lipid which are anchored in the cell membrane of the cell. Said method comprises isolating at least a single target cell from a multitude of cells by applying the screening method according to any of the embodiments described above and cultivating it.

Advantageously, isolating a target cell allows for establishing a cell line in order to either produce a certain biomolecule (antibody, growth factor/cytokine, enzyme . . . ) or to provide a cell model for studying effects of an active substance (drug research). To study the effect of a certain molecule or substance, clonal selection of cells is advantageous. The fluorescent sialic acid-specific can be used as such tool to specifically separate cells with high expression of sialic acid.

According to an embodiment in the production method the target cell is a specific immunoglobulin-producing cell or specific cytokine-producing cell.

Advantageously immunoglobulins can be used both in diagnostic and therapeutic applications. Cytokines can be used both for stimulating certain cell lines in a cell culture, e.g. in biotechnology, or for treating a condition. To study a certain cell line, clonal selection of cells is advantageous. The fluorescent sialic acid-specific can be used as such tool to specifically separate cells with high expression of sialic acid.

According to an embodiment a use of a double fluorescent particle as described above for in vitro identification and/or characterization of circulating tumor cells in a blood sample is suggested.

Advantageously, ratiometric dual-signal measurements can efficiently improve the accuracy and sensitivity of an assay. Such measurements largely avoid intensity fluctuations because of output power fluctuations of the excitation source, defocusing effects or photobleaching.

According to an embodiment a use of a double fluorescent particle as described above for identifying a cell, a cell line, or a hybridoma is suggested, wherein the cell, the cell line, and the hybridoma produces a specific immunoglobulin or a specific cytokine.

Advantageously, cell lines, especially hybridoma cell lines are used to permanently produce a certain compound which is generated by biosynthesis in the cell and advantageously released into the culture medium. To use cells, cell lines, or hybridomas, clonal selection of cells is advantageous. The fluorescent sialic acid-specific can be used as such tool to specifically separate cells with high expression of sialic acid.

According to an embodiment an imaging technique for cancer detection in a tissue is suggested. The suggested imaging technique comprises: detecting a fluorescence ratio at a double fluorescent particle and generating an image of the tissue comprising cells, wherein cells with a surface structure recognized by double fluorescing particles according to any of claims 1 to 8 are highlighted against a background of the image.

Advantageously, such images can be used for detection of cancer cells within the tissue. A tissue normally comprise of several different types of cells, both normal cells and the tumor of interest. Optimally, the tumor cells express more sialic acid and can be distinguished from the normal cells with use of the double fluorescent particles, due to a higher binding ratio and measured fluorescence.

According to an embodiment in the suggested imaging technique the tissue comprises a histological sample which is studied in vitro. Therein, the tissue may have been obtained, e.g., by a needle biopsy.

Advantageously, malign tissue can be identified, a therapeutic agent and/or a therapy can be evaluated and the prognosis for a patient can possibly be improved.

According to an embodiment a cell sorting technique is suggested, the technique comprising: labelling a cell with the double fluorescent particle as suggested above (and described herein), detecting a ratio of first and second fluorescence signals; and registering the presence of a cell which is labelled by the double fluorescent particle. Optionally the cell sorting technique may comprise selectively collecting registered cells, wherein cells carrying identical particles or sets of particles are sorted and/or collected.

Advantageously, specific cells, e.g. tumor indicating cells which are contained in a blood sample can be reliably detected. Thus, a diagnosis can be verified or a therapy be started for a patient with circulating cells of a certain type.

According to an embodiment in the suggested cell sorting technique the molecularly imprinted polymer of the polymer shell of the double fluorescent particle is adapted to recognize a certain cell surface structure, in particular a glycosylated membrane anchored molecule, e.g. a CD structure or a tumor marker. As can be contemplated by the skilled person, a combination of different double fluorescent particles, comprising different combinations of first and second fluorescences, each combination being characterized by a certain specificity of the MIP shell can be used as well. Thus, certain combinations of cell surface markers on a cell can reliably be detected. The double fluorescent particles can be applied together with other labels or particles, e.g. in a multiplex assay.

Typically glycosylated structures, e.g. proteins or lipids comprising, e.g., a sialic acid derivative are known as tumor markers. Their reliable detection can thus be useful. Sialic acid is a generic term for the N- or O-substituted derivatives of neuraminic acid, a monosaccharide with a nine-carbon backbone. It is also the name for the most common member of this group, N-acetylneuraminic acid (Neu5Ac). Sialic acids are found widely distributed in animal tissues and to a lesser extent in other organisms, ranging from plants and fungi to yeasts and bacteria, mostly in glycoproteins and gangliosides, which occur at the end of sugar chains connected to the surfaces of cells and soluble proteins.

Each of the embodiments described above may be combined with any other embodiment or embodiments unless clearly indicated to the contrary.

Dual fluorescent reporter particles for detection of tumor markers comprising a fluorescent core and a differently fluorescent MIP shell allow ratiometric dual-signal measurements. Such measurements can efficiently improve the accuracy and sensitivity of corresponding sensing applications. By rationally designing new MIP-type probes, e.g. with layer-by-layer assembly (electrostatic layer-by-layer-deposition) or with core/shell structures, comprising two or more types of probe molecules (each having characteristic fluorescence properties) can be loaded into different compartments of the core/shell structure, respectively. After facile combination of fluorescent MIP layers atop of fluorescent cores, MIP-based recognition and imaging probes can be tailored for specific applications. These core/shell particles, i.e. double fluorescent particles, allow for quantitative multiplexed sensing of target molecules either expressed by live or fixed cells (and tissues) or attached to solid surfaces. Typically, the target molecules are biomolecules, such as membrane proteins or lipids. Preferably, the biomolecules comprise oligosaccharides which are attached at certain amino acid residues of the membrane protein or at certain structures of a membrane-anchored lipid. The oligosaccharides thus anchored to the outside of the cell membrane are important for biological processes such as cell adhesion or cell-cell interactions. Particularly, glycosphingolipids play an important role in oncogenesis and ontogenesis and hence are important to monitor with a suitable assay.

Applications of the suggested double fluorescent particles in cell culture and cancer research embrace both migration and viability assays. Further, immunohistochemical labeling can be improved by enhanced selectivity and sensitivity provided by the double fluorescent particles in different multiplex formats. In diagnostics and drug research that allows for detection of circulating tumor cells, i.e. metastasising solid tumors.

Applications of the double fluorescent particles and imaging techniques based thereon are suggested both for clinical practice and drug research, e.g. using mouse models, and cell culture.

Multiplex assay with colour-coded beads for differentiating cells expressing different biomarkers. Improved stability of tumor marker detection since MIP particles are easier to store and handle compared to antibodies. Ease in production compared to conventional methods for antibody preparation, specifically against glycosylated proteins.

Small-sized (lower than 100 nm) dual emitting (blue+yellow or red+yellow, etc.) MIP-type probes offer bright signals in microscopy and cytometry. In principle, the suggested particles are designed for applications with all common laser/laser diode excitation wavelengths and emission filter settings that are usually available in commercial fluorescence microscopes and cytometers. There are no true preferences, because if, for instance, a co-staining of cell organelles (see DAPI example in FIGS. 18 and 19) is necessary, optimal wavelength windows of the double fluorescent particles can again be different than for application of the particles alone.

Europium and terbium as used in the present application for generating a first fluorescence, i.e. a fluorescence of the core, is selected according to the table below.

|  | Europium salts * | Terbium salts * |
|---|---|---|
| $EuX_3$ or $TbX_3$ | Europium(III) fluoride, Europium(III) chloride, Europium(III) bromide, Europium(III) iodide | Terbium(III) fluoride, Terbium(III) chloride, Terbium(III) bromide, Terbium(III) Iodide |
| $EuX_2$ or $TbX_2$ | Europium(II) fluoride, Europium(II) chloride, Europium(II) bromide, Europium(II) iodide | Terbium(II) fluoride, Terbium(II) chloride, Terbium(II) bromide, Terbium(II) iodide |
| Oxide | Europium(III) oxide | Terbium(III) oxide, Terbium(III, IV) oxide |
| Carboxylate | Europium(III) acetate, Europium(III) nitrate, Europium(III) trifluoromethanesulfonate, Europium(III) Sulfate | Terbium(III) acetate, Terbium(III) nitrate, Terbium(III) trifluoromethanesulfonate, Terbium(III) Sulfate |
| Organic ligand | Europium(III) acetylacetonate, Europium(III) tris[3-(heptafluoropropylhydroxymethylene)-(+)-camphorate], Europium(III) tris[3-(trifluoromethylhydroxymethylene)-(+)-camphorate], Europium(III) tris[3-(heptafluoropropylhydroxymethylene)-d-camphorate], Europium(III) tris[3-(heptafluoropropylhydroxymethylene)-(−)-camphorate], Europium(III) tris(1,3-diphenyl-1,3-propanedionato) mono(5-amino-1,10-phenanthroline), Europium(III) tris(1,3-diphenyl-1,3-propanedionato) | Terbium(III) acetylacetonate, Terbium(III) tris[3-(heptafluoropropylhydroxymethylene)-(+)-camphorate], Terbium(III) tris[3-(trifluoromethylhydroxymethylene)-(+)-camphorate], Terbium(III) tris[3-(heptafluoropropylhydroxymethylene)-d-camphorate], Terbium(III) tris[3-(heptafluoropropylhydroxymethylene)-(−)-camphorate], |

-continued

| Europium salts * | Terbium salts * |
|---|---|
| mono(1,10-phenanthroline),<br>Europium(III) tris(2,2,6,6-tetramethyl-3,5-heptanedionate),<br>Europium(III) tris(1,1,1,2,2,3,3-heptafluoro-7,7-dimethyl-4,6-octanedionate)<br>Tris(benzoylacetonato) mono(phenanthroline)europium(III),<br>Tris(tetramethylcyclopentadienyl)europium(III),<br>Tris[N,N-bis(trimethylsilyl)amide]europium(III) | Terbium(III) tris(1,3-diphenyl-1,3-propanedionato) mono(5-amino-1,10-phenanthroline),<br>Terbium(III) tris(1,3-diphenyl-1,3-propanedionato) mono(1,10-phenanthroline),<br>Terbium(III) tris(2,2,6,6-tetramethyl-3,5-heptanedionate),<br>Tris(benzoylacetonato) mono(phenanthroline) terbium(III),<br>Tris(tetramethylcyclopentadienyl)terbium(III),<br>Tris[N,N-bis(trimethylsilyl)amide]terbium(III) |

* All the listed salts' hydrate derivatives are also included

Advantageously, these lanthanides can be introduced into silica nanoparticles forming the core using a microemulsion method, e.g. as chloride salts. The dyes above comprise emitters which can be conveniently detected by conventional bioanalytical and diagnostic instrumentation.

According to typical embodiments, a rare earth metal-doped (first fluorescence) silica core can be covered by a fluorescent (second fluorescence) MIP shell which integrates a fluorescent monomer.

Dyes which can be used for the suggested steric staining of a silica core are selected from the list below:
Rhodamine and derivatives,
Fluorescein and derivatives,
Tris(bipyridine)ruthenium(II) chloride and derivatives,
Tris(bipyridine)osmium(II) hexafluorophosphate and derivatives,
Sulphorhodamine B and derivatives,
Sulphorhodamine G and derivatives,
Sulphorhodamine 101 and derivatives,
Styryl dyes,
Oxazine derivatives, and
Metallo-porphyrin derivatives.

The dyes above are advantageously charged, that is exist and can be used as salts with a large variety of counterions ranging from sodium, potassium or ammonium (for anionic dyes) to chloride, bromide, iodide, perchlorate, hexafluorophosphate or tetrafluoroborate (for cationic dyes) and therefore can be doped sterically into the silica core.

Dyes which are used for the suggested covalent staining of a silica core after having been conjugated to a silane derivative which is used for generating the silica core are selected from the list below:
Coumarin and derivatives,
Rhodamine and derivatives,
Fluorescein and derivatives,
Tris(bipyridine)ruthenium(II) chloride and derivatives,
Tris(bipyridine)osmium(II) hexafluorophosphate and derivatives,
Sulphorhodamine B and derivatives,
Sulphorhodamine G and derivatives,
Sulphorhodamine 101 and derivatives,
BODIPY dyes and derivatives,
Naphthalimide and benzoxazole derivatives,
Styryl dyes,
Pyrromethane dyes,
Pyridine derivatives,
Oxazine derivatives,
Porphyrin derivatives, and
Metallo-porphyrin derivatives.

The dyes above are linked to at least one silane derivative which is used to generate the silica core.

A main advantage of the proposed embodiments is that a new tool for cell biology is provided.

FIG. 1 shows the generation of a double fluorescent particle as described in example 1, i.e. a particle comprising a fluorescent carbon nanodot core having a silica structural shell which is covered by a fluorescent molecularly imprinted polymer (MIP) shell. Such particle is abbreviated herein as CND@SiO$_2$@MIP.

Figure 2:
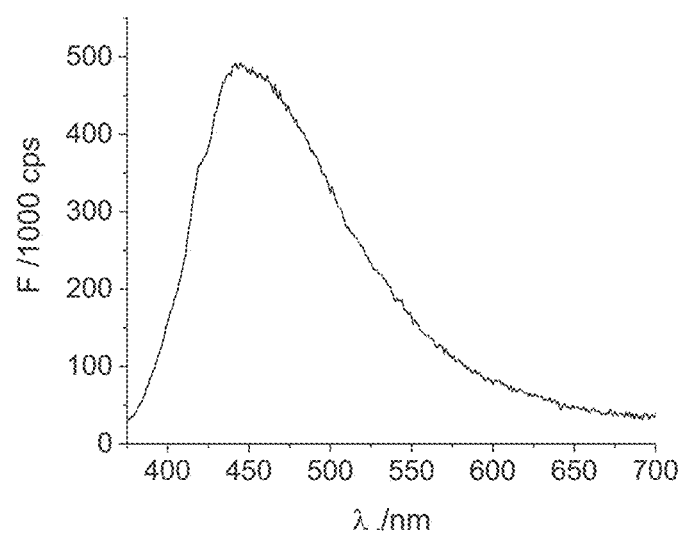
FIG. 2 shows a fluorescence spectrum of CNDs in ethanol.

Further, FIG. 2 shows a representative fluorescence spectrum of CNDs in ethanol.

Figure 3:
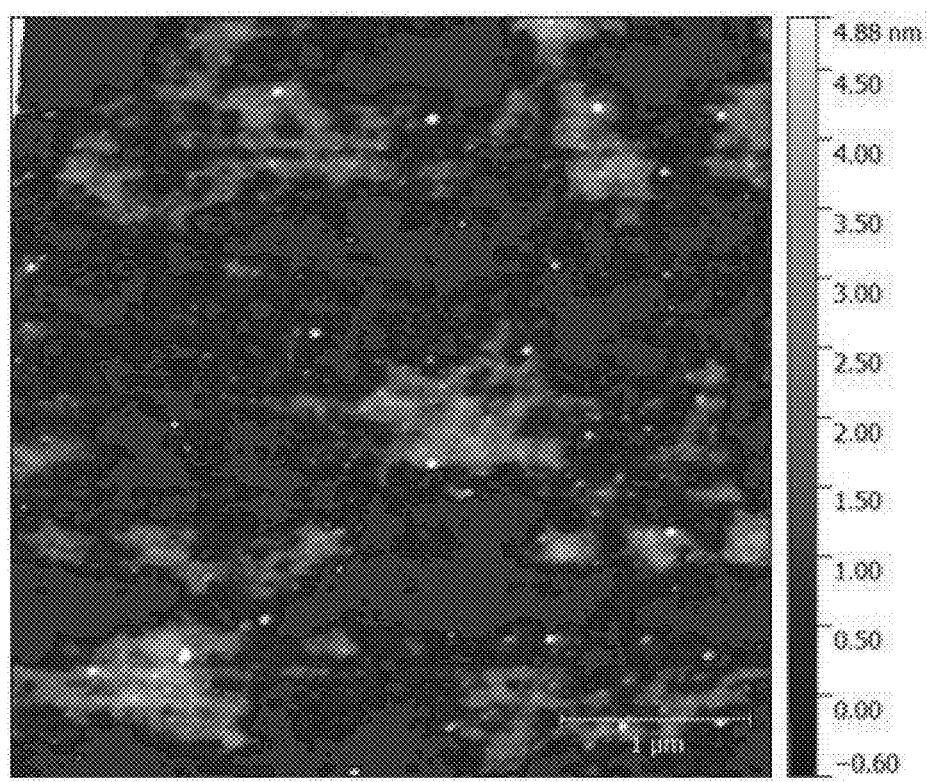
FIG. 3 shows an AFM image (tapping mode) of carbon nanodots which have been used as cores for the double fluorescent particles.

In FIG. 3 AFM images of CNDs as used for cores of the CND@SiO$_2$@MIP are shown. The CNDs have been deposited on a silicon wafer. The bright, approximately 5 nm high dots are CNDs.

Figure 4:
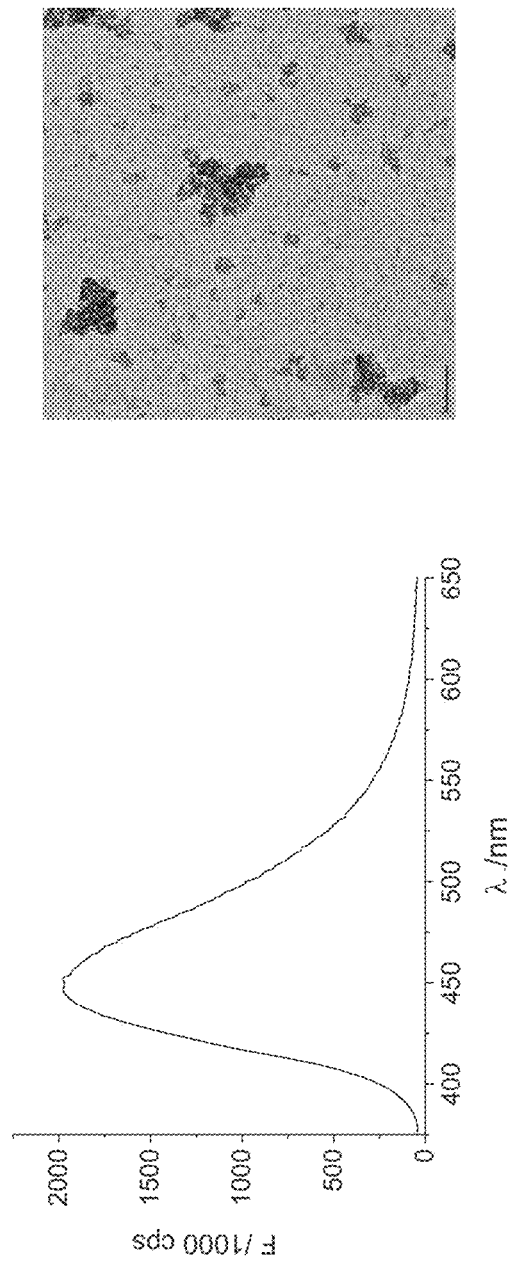
FIG. 4 shows a fluorescence spectrum in water (left) and a TEM image (right) of CND@SiO$_2$; scale bar=200 nm.

FIG. 4 shows the fluorescence spectrum in water (left) and a TEM image (right) of CND@SiO$_2$; scale bar=200 nm.

Figure 5:
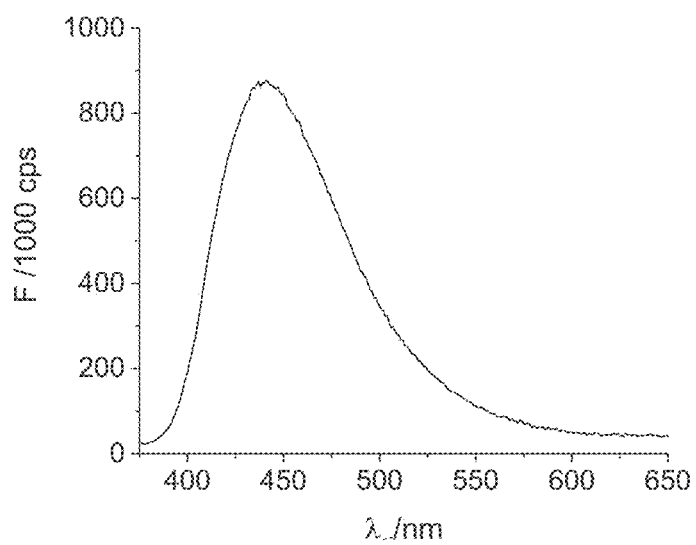
FIG. 5 shows the fluorescence spectrum of CND cores which have been covered with a structural SiO$_2$ shell, wherein the shell was modified with (3-aminopropyl)triethoxysilane (APTES) in order to prepare particles according to example 1.

FIG. 5 shows a fluorescence spectrum as recorded of CND@SiO$_2$-APT which were suspended in water.

Figure 6:
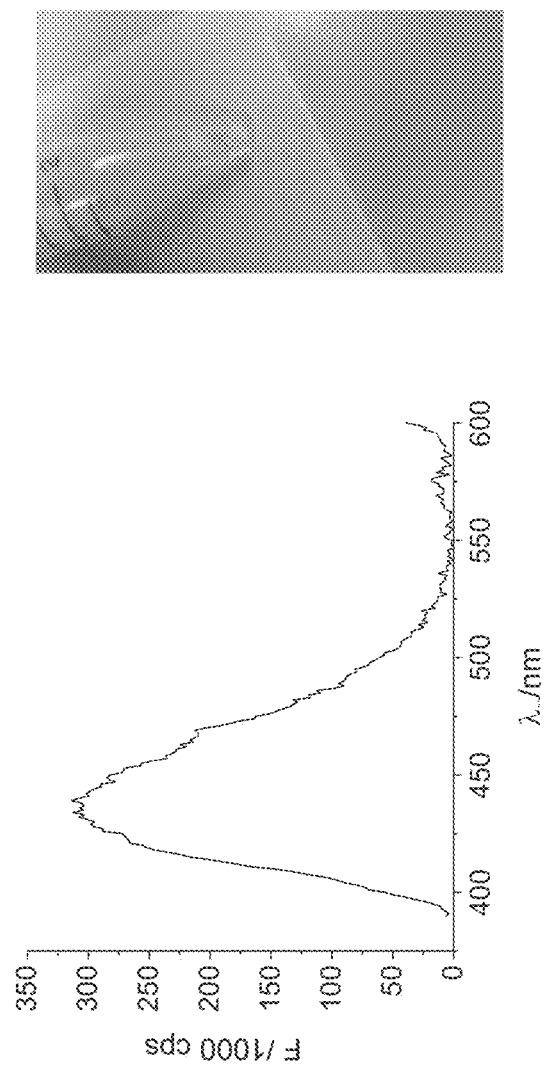
FIG. 6 shows a fluorescence spectrum and the macroscopic appearance of CND@SiO$_2$-RAFT.

FIG. 6 shows the fluorescence spectrum (in water) of CND@SiO$_2$ which have been modified with 4-cyano-4-(phenylcarbonothioylthio)pentanoic acid (CPBA) to yield CND@SiO$_2$-RAFT as described for example 1. The photograph of CND@SiO$_2$-RAFT on the right shows the typical pink color of the RAFT agent.

Figure 7:
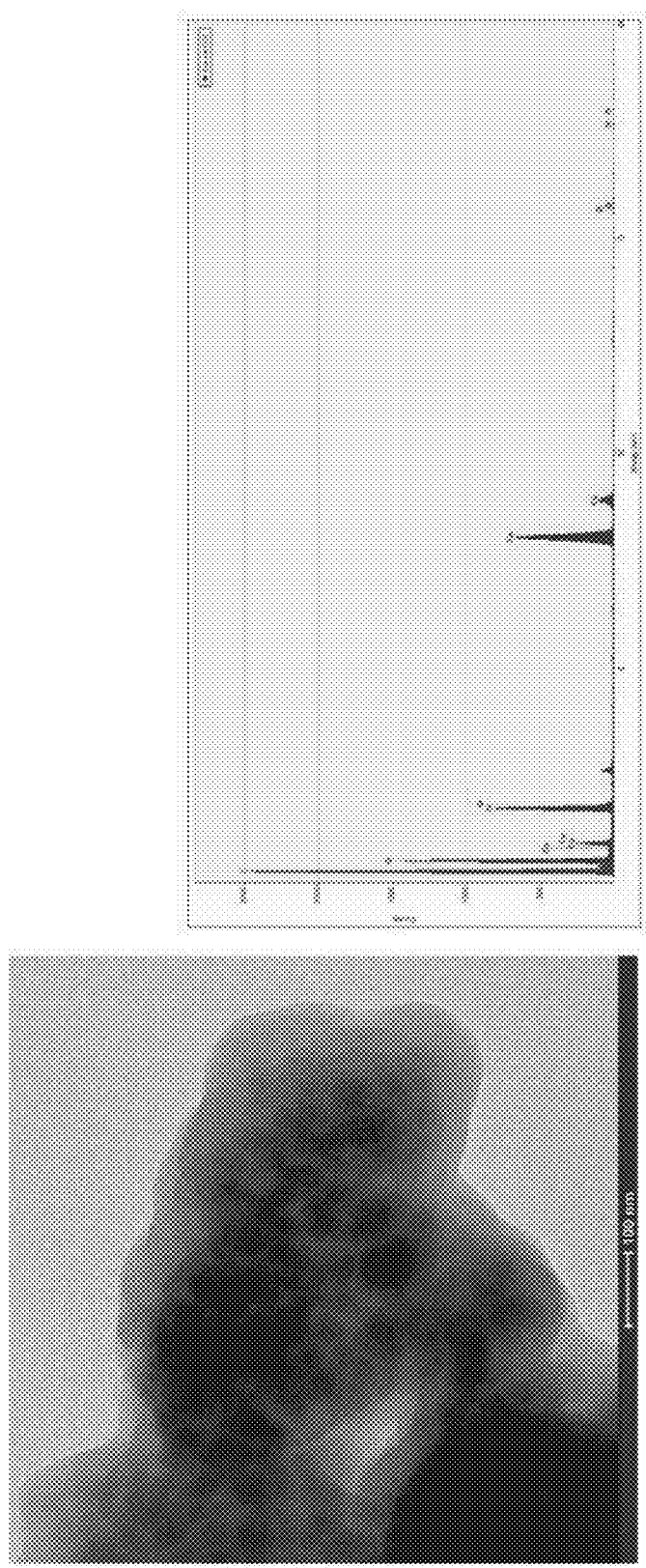
FIG. 7 shows a TEM image and the corresponding EDX spectrum of CND@SiO$_2$@MIP particles according to example 1.

FIG. 7 shows a TEM image of a representative batch of doped CND@SiO$_2$@MIP particles imprinted with SA. The right image shows the corresponding EDX spectrum.

Figure 8:
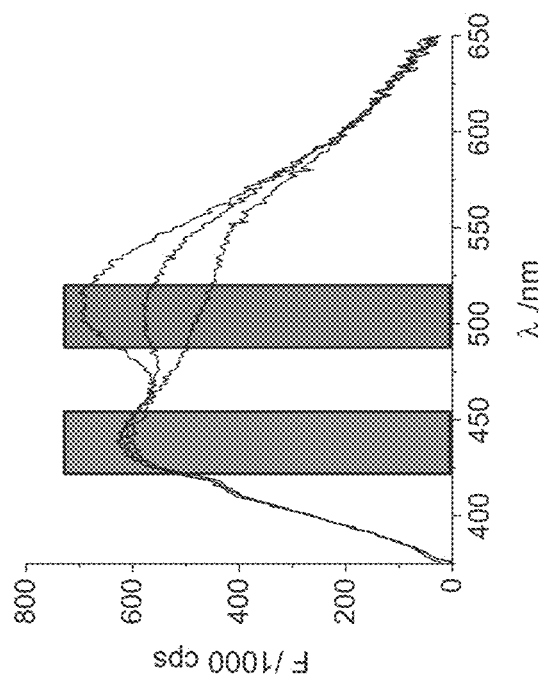
FIG. 8 shows the double fluorescence signal of CND@SiO$_2$@MIP in methanol (left) and that of a second CND@SiO$_2$@MIP in the presence of different concentrations of deprotonated sialic acid in chloroform (right).
Figure 8:
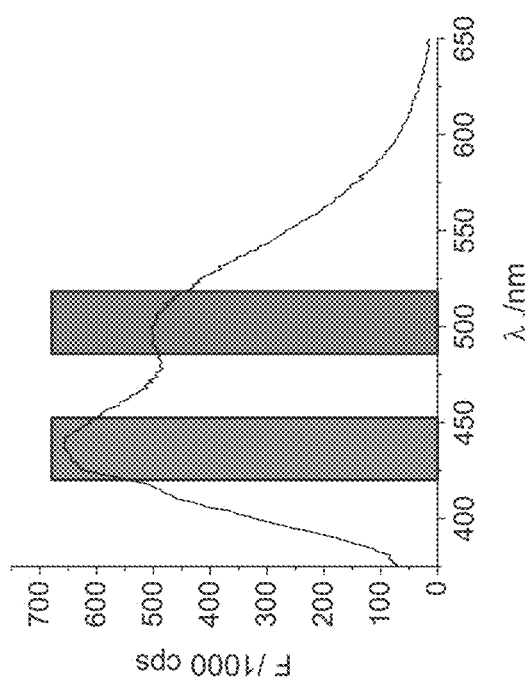

FIG. 8 shows the double fluorescence signal of CND@SiO2@MIP in methanol (left) and that of a second CND@SiO2@MIP in the presence of different concentrations of deprotonated sialic acid in chloroform (right).

Figure 9:
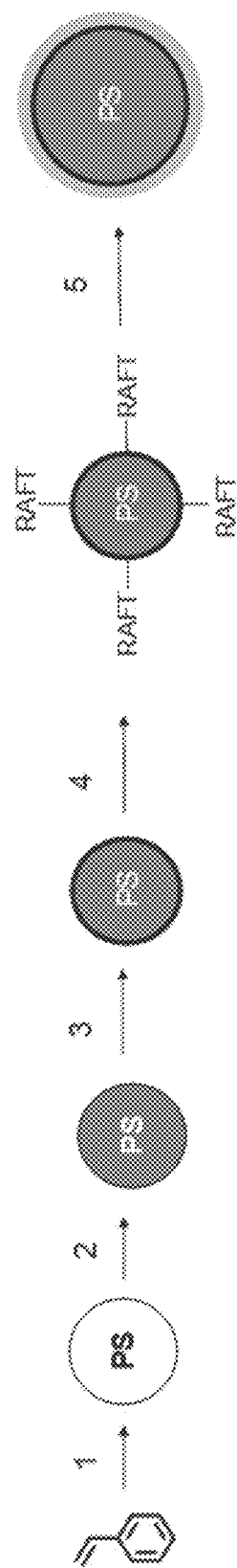
FIG. 9 is a schematic representation of the method for obtaining fluorescent polystyrene core/silica structural shell/fluorescent MIP shell particles (PS@SiO$_2$@MIP) according to example 2.

FIG. 9 illustrates the synthetic path to and architecture of PS@SiO$_2$@MIP as described under example 2, comprising the steps: polymerization of styrene (1); dye doping of polystyrene (PS) (2); silica coating of PS (3); introduction of amino and RAFT groups to silica coating (4); and preparation of fluorescent imprinted polymer layer (5).

Figure 10:
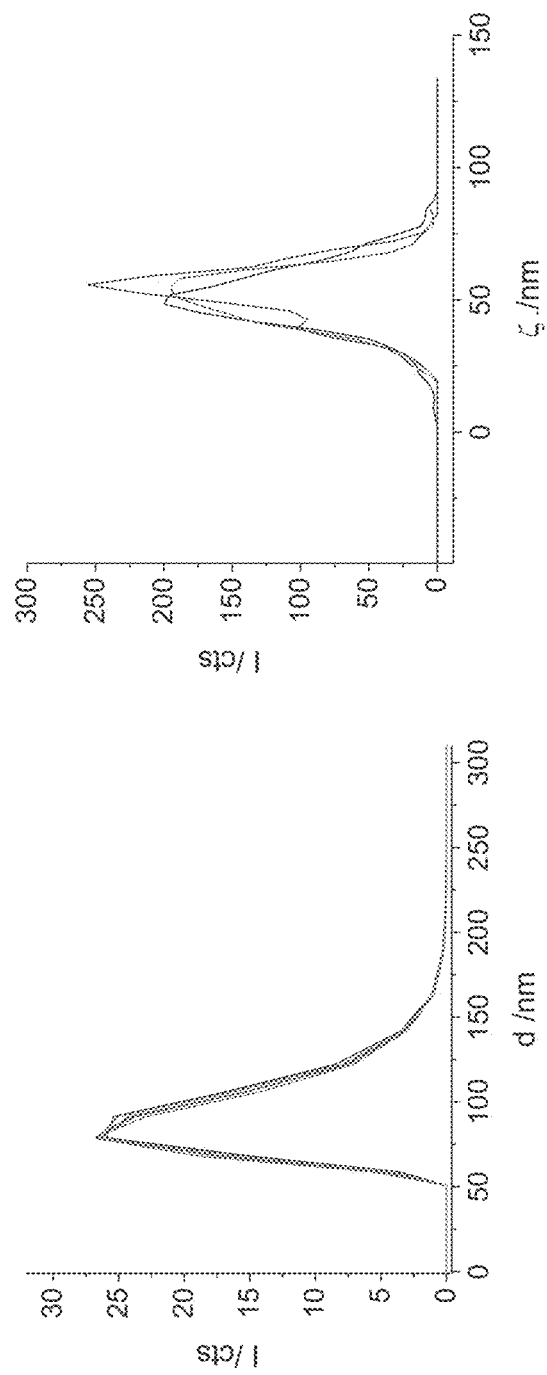
FIG. 10 illustrates the particle size (polydispersity) and zeta-potential of polystyrene (PS) cores as used for double fluorescent particles according to example 2 described below.

In FIG. 10 on the left hand, the size distribution for PS core formation is shown for six different repetitions of reaction solutions after 5.5 hours. The graph on the right shows zeta potential measurements of three different batches. In particular, the particle sizes of various batches of PS cores have been determined by dynamic light scattering, average diameter 89.7±21.1 nm. The polydispersity index (PDI) was ≤0.04. The right graph shows corresponding zeta potentials (average+52.7 mV), indicating the net positive surface charge of the PS cores.

Figure 11:
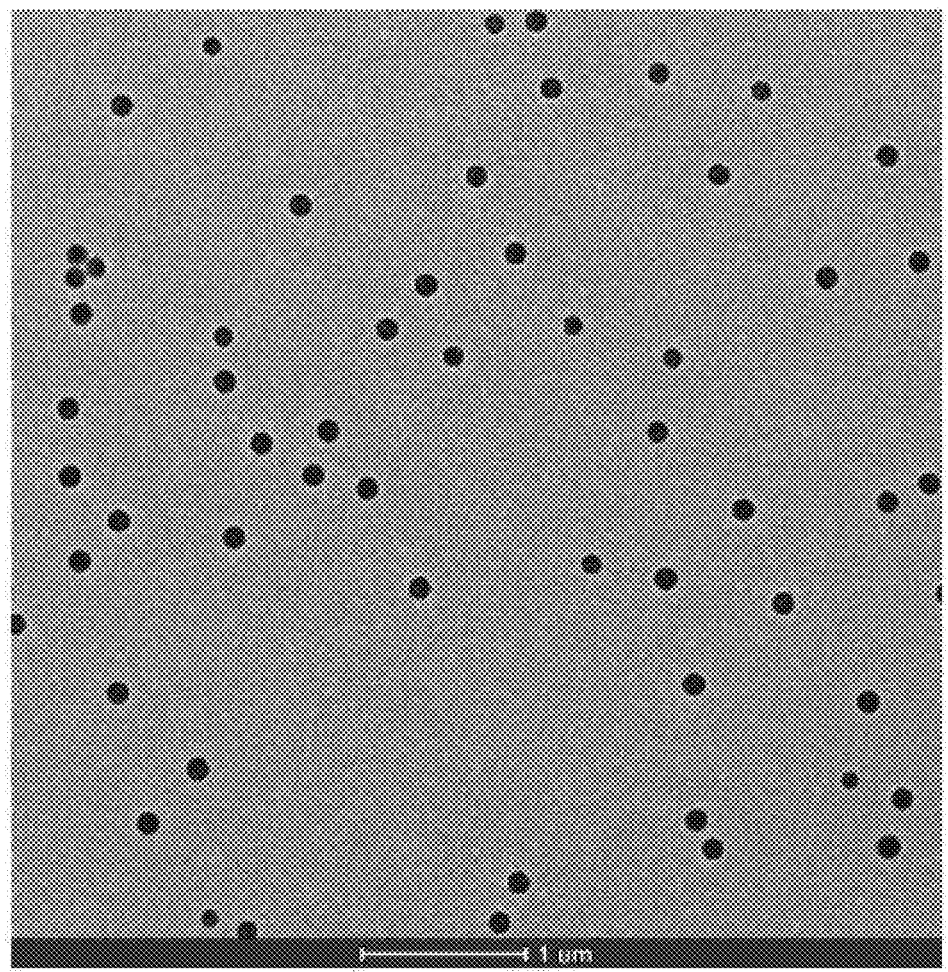
FIG. 11 illustrates a TEM image of representative polystyrene cores as used for particle preparation.

FIG. 11 shows a TEM image of representative polystyrene cores as used for particle preparation.

Figure 12:
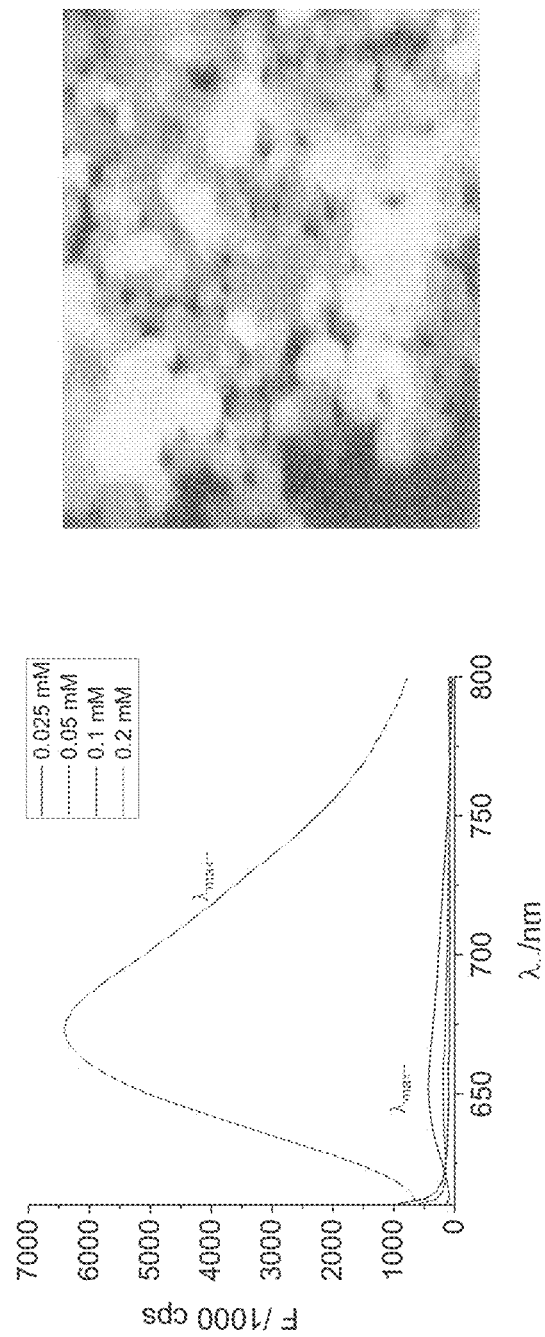
FIG. 12 shows fluorescence emission spectra (left) and a microscopic image (right) of dye-doped PS cores.

In particular, FIG. 12, left shows the fluorescence emission spectra of PS cores doped with dye II, suspended in 0.5% surfactant solution (Brij® L23), as a function of dye concentration in the doping solution. On the right, a fluorescence microscopy image of PS particles with different dye contents as indicated and recorded with 460-495 nm bandpass filter in excitation and 510 nm long pass filter in emission are shown.

Figure 13:
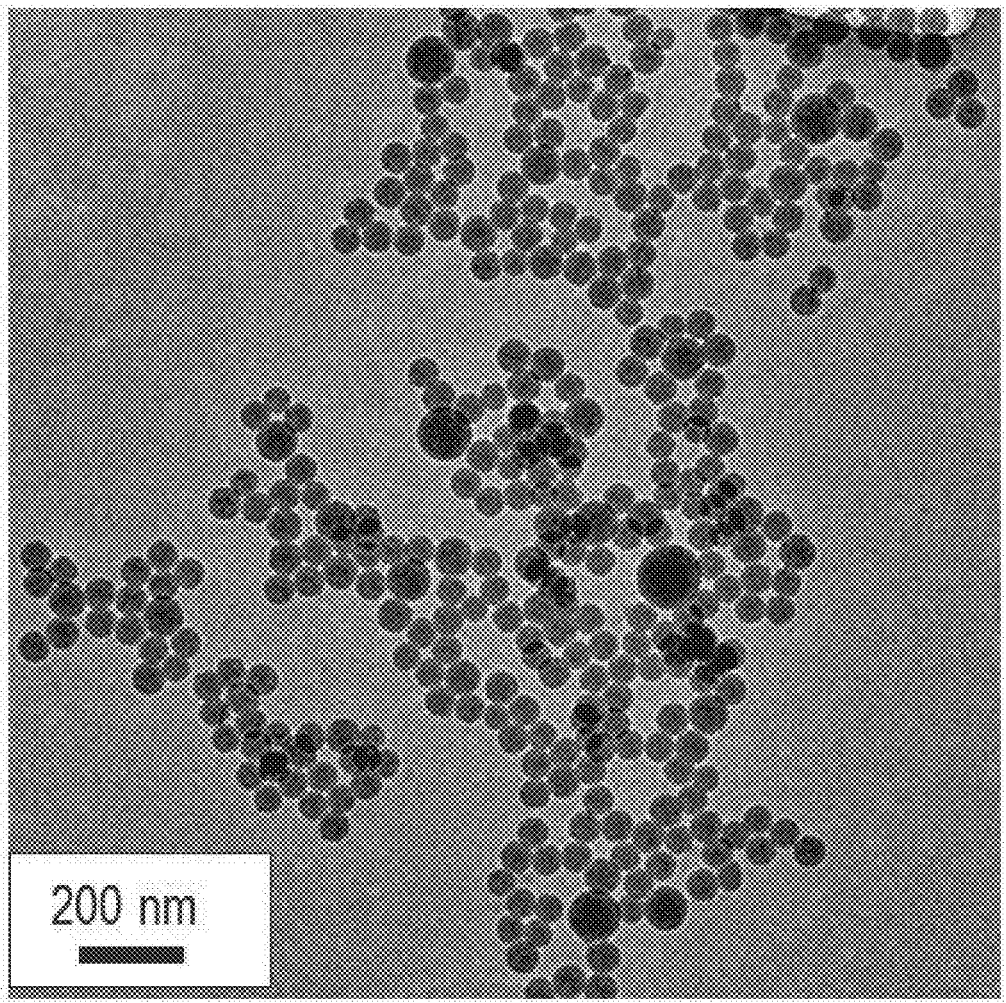
FIG. 13 shows a TEM-image of a representative batch of dye-doped PS cores.

FIG. 13 is a TEM-image of a representative batch of dye-doped PS cores, i.e. PS particles which have been doped with dye II as indicated below.

Figure 14:
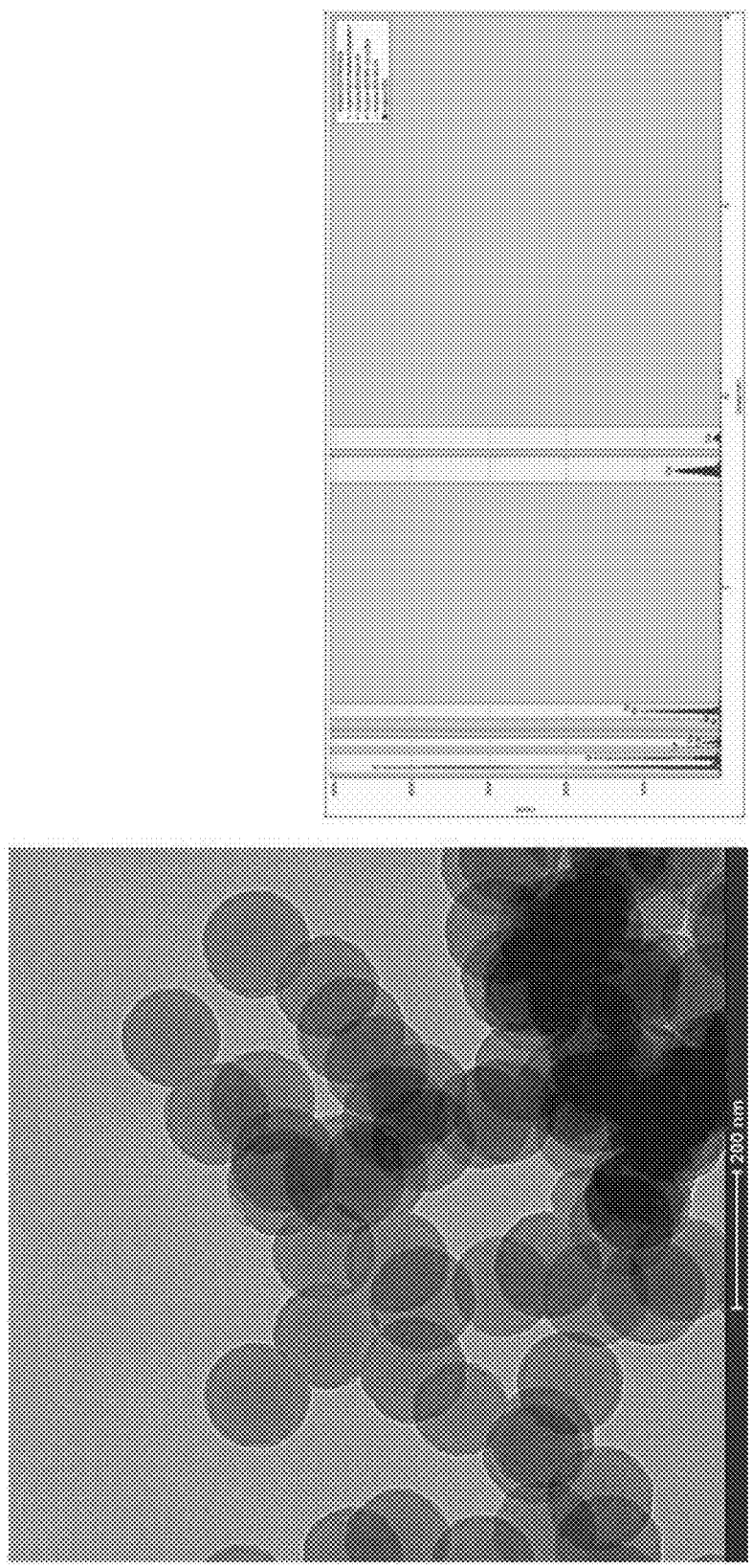
FIG. 14 shows on the left a TEM image of a representative batch of dye-doped PS@SiO$_2$ particles and on the right a corresponding EDX spectrum.

FIG. 14 shows on the left a TEM image of a representative batch of PS@SiO$_2$ particles and on the right a corresponding EDX spectrum.

Figure 15:
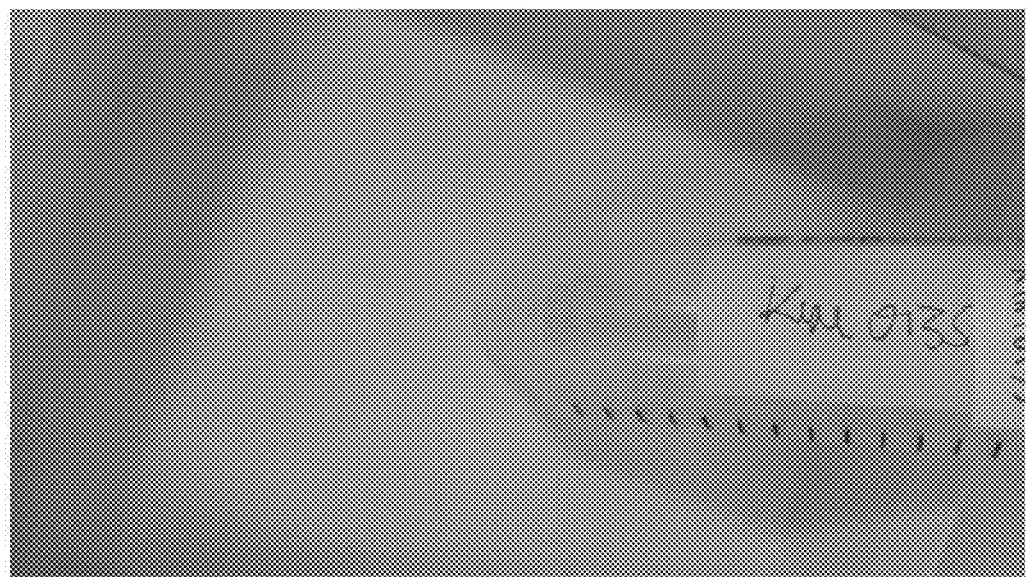
FIG. 15 is a photograph of the RAFT agent-modified PS@SiO$_2$-APT, i.e. of PS@SiO$_2$-RAFT particles.

FIG. 15 is a photograph of the RAFT agent-modified PS@SiO$_2$-APT, showing the typical pink color of the RAFT agent. The modification yields PS@SiO$_2$-RAFT particles.

Figure 16:
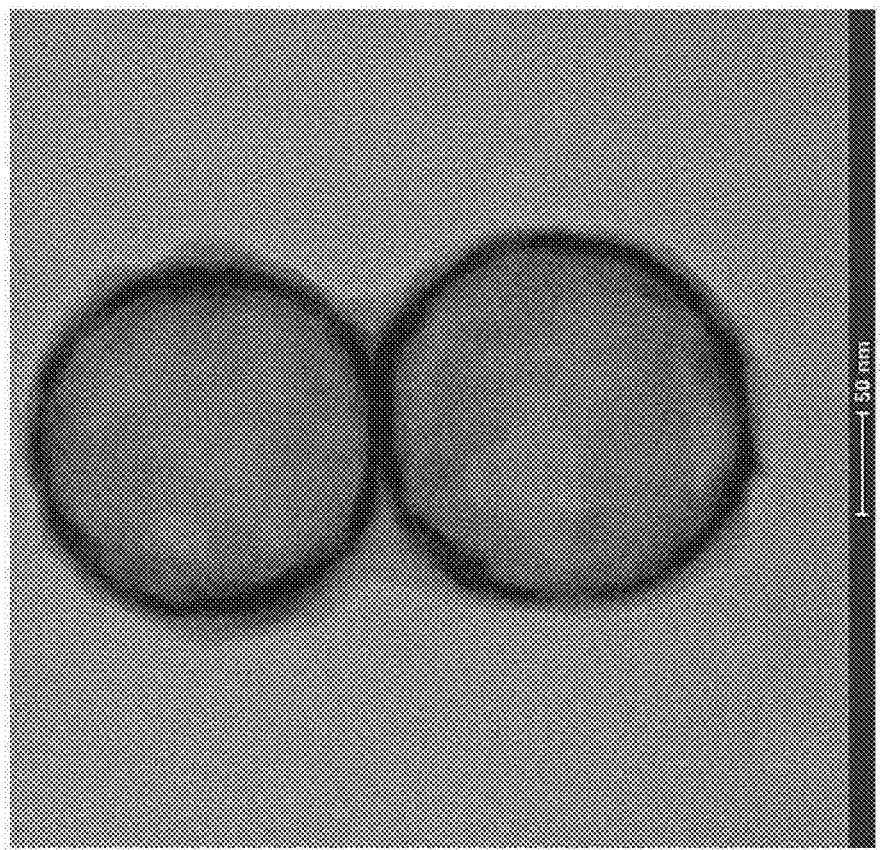
FIG. 16 shows two TEM images of a representative batch of PS@SiO$_2$@MIP particles.
Figure 16:
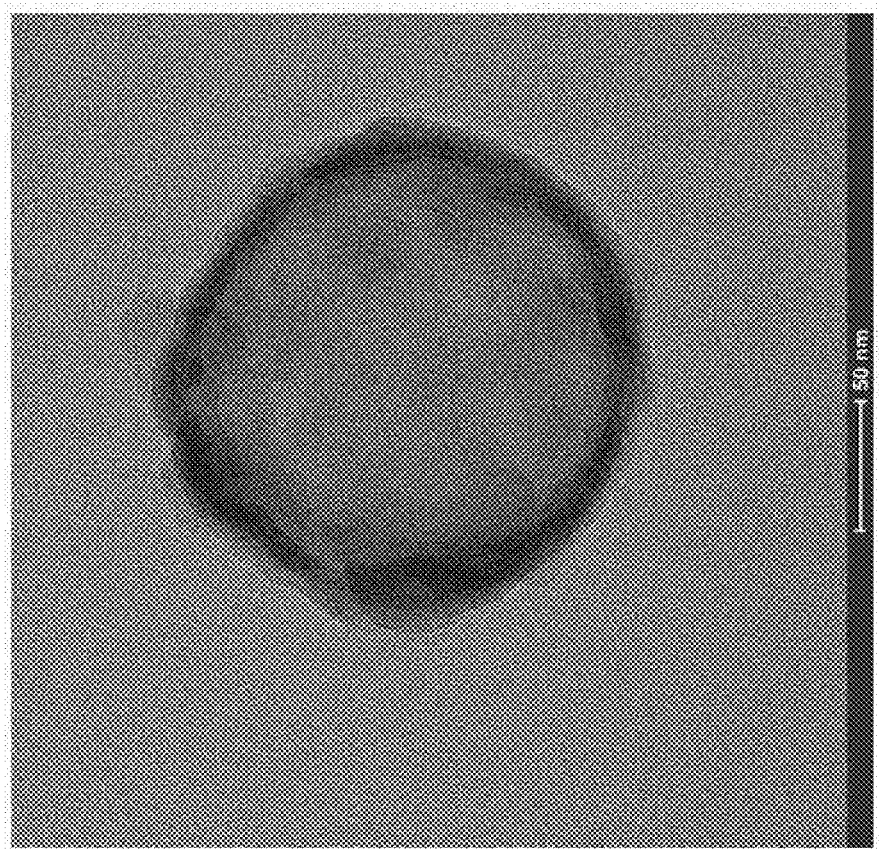

FIG. 16 shows two representative TEM images of PS@SiO$_2$@MIP particles comprising both a fluorescent core and a fluorescent MIP layer. As described further below, the MIP was generated with sialic acid (SA) as a template.

Figure 17:
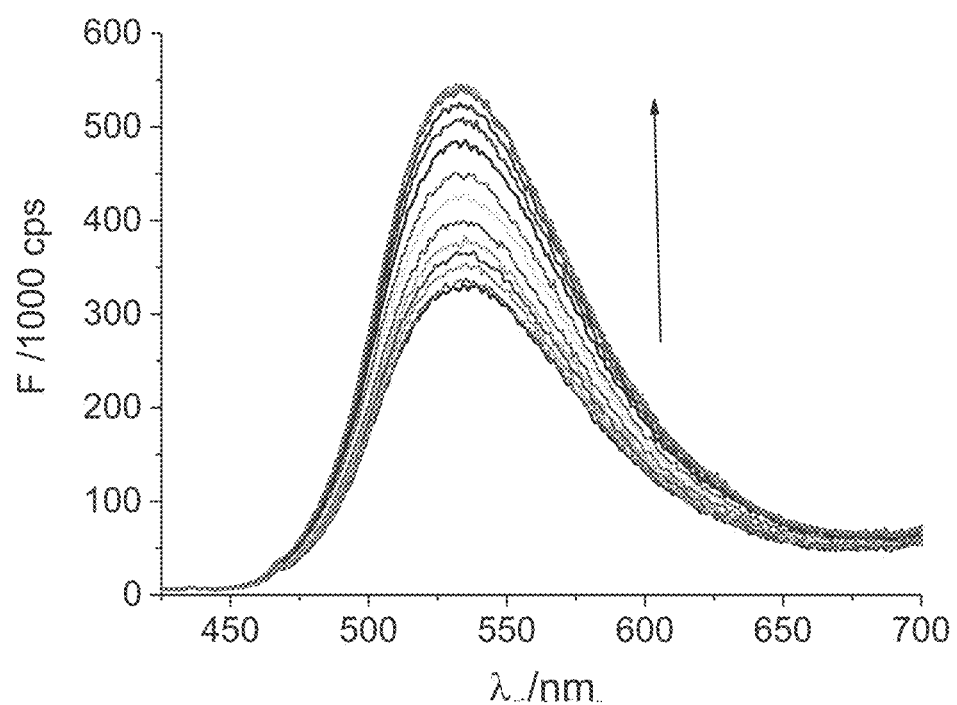
FIG. 17 illustrates a fluorescence titration of PS@SiO$_2$@MIP, imprinted with sialic acid (SA), upon addition of increasing amounts of SA in dimethylformamide.

FIG. 17 illustrates a fluorescence titration of PS@SiO$_2$@MIP, imprinted with sialic acid (SA), upon addition of increasing amounts of SA in dimethylformamide. The figure shows an increase of the MIP's fluorescence upon addition of increasing amounts of sialic acid to the solution.

Figure 18:
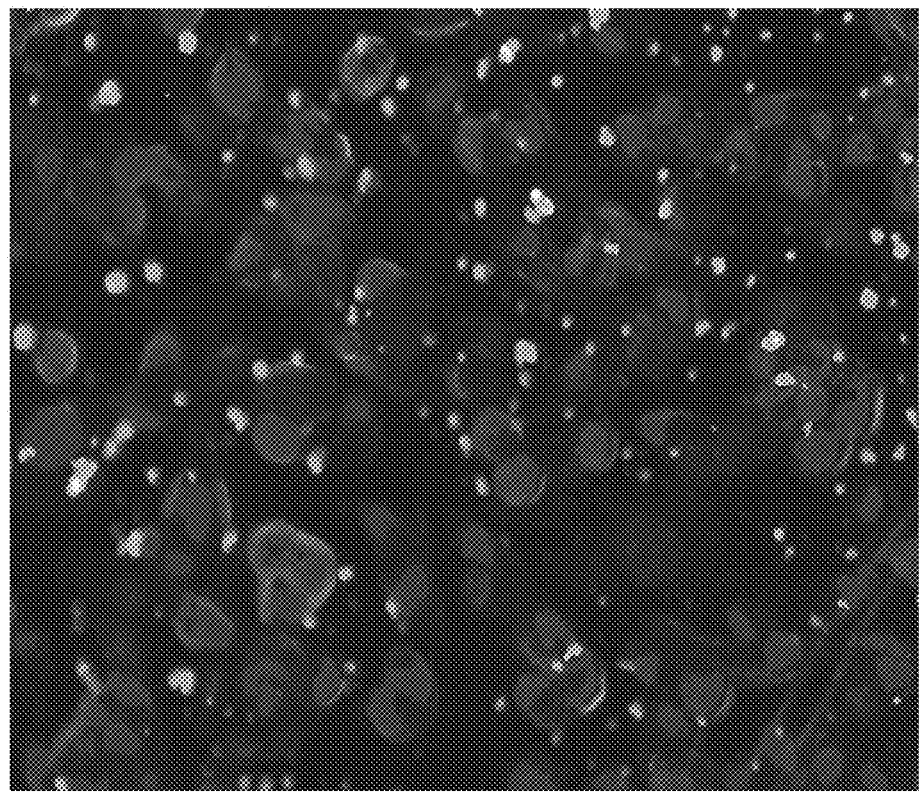
FIG. 18 shows a fluorescence microscopy image of the human breast cancer cell line MDA-MB 231 as stained with 150 µg/ml MIP particles.

FIG. 18 shows a monolayer of human breast cancer cells (MDA-MB 231). After incubation of the cells with 150 µg/ml MU MIPs and subsequent washing apparently >50% of the cells have been selectively marked. The green fluorescence is from the bound sialic acid-specific particles. The nuclei are stained with DAPI, which gives a blue color.

Figure 19:
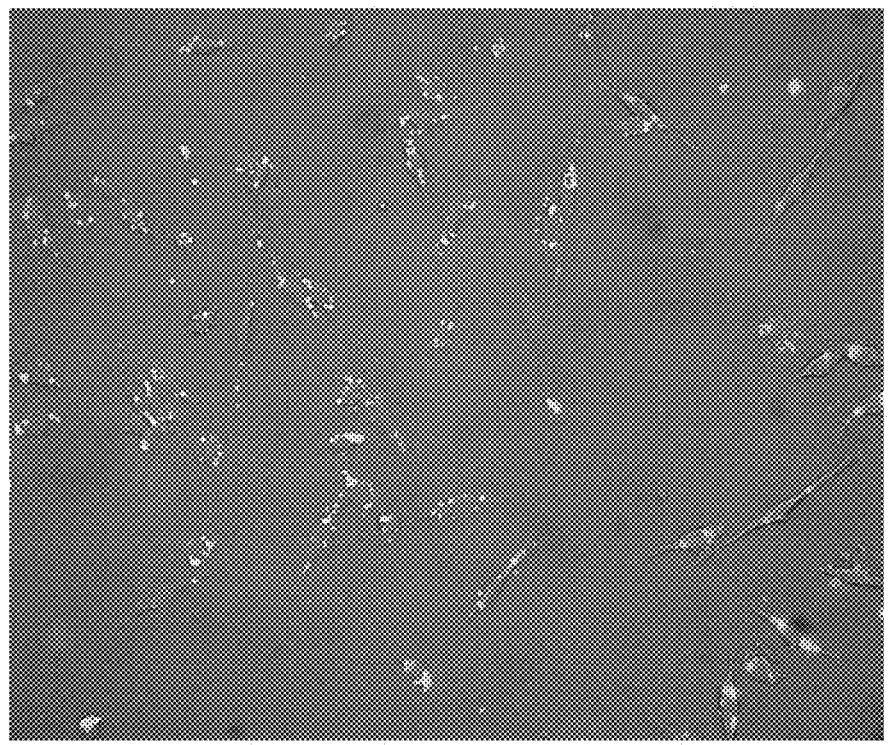
FIG. 19 shows a fluorescence microscopy/phase contrast image of murine macrophage cells (RAW 264.7) which have been incubated with 0.4 mg/ml SA-MIPs.

FIG. 19 shows a fluorescence microscopy/phase contrast image of cells of the murine macrophage cell line RAW 264.7 s which have been incubated with 0.4 mg/ml BAM SA-MIPs. Mouse macrophage RAW264.7 cells were incubated in a tube with 0.4 mg/ml of SAMIPs. The unbound SAMIPs were "size separated" directly after staining by centrifugation at a lower speed (20×g). By that, many unbound SAMIPS can be removed for improving analysis of the samples. In this case, the RAW264.7 cells that bound the SAMIPs were further cultured in a dish before analysis. They were allowed to adhere overnight and the bound SAMIPs were probably also internalized by the macrophages (see image). The nuclei are stained with DAPI, which gives a blue color. The green fluorescence is from the bound and to some extent ingested sialic acid-specific particles. The nuclei are stained with DAPI, which gives a blue color.

Figure 20:
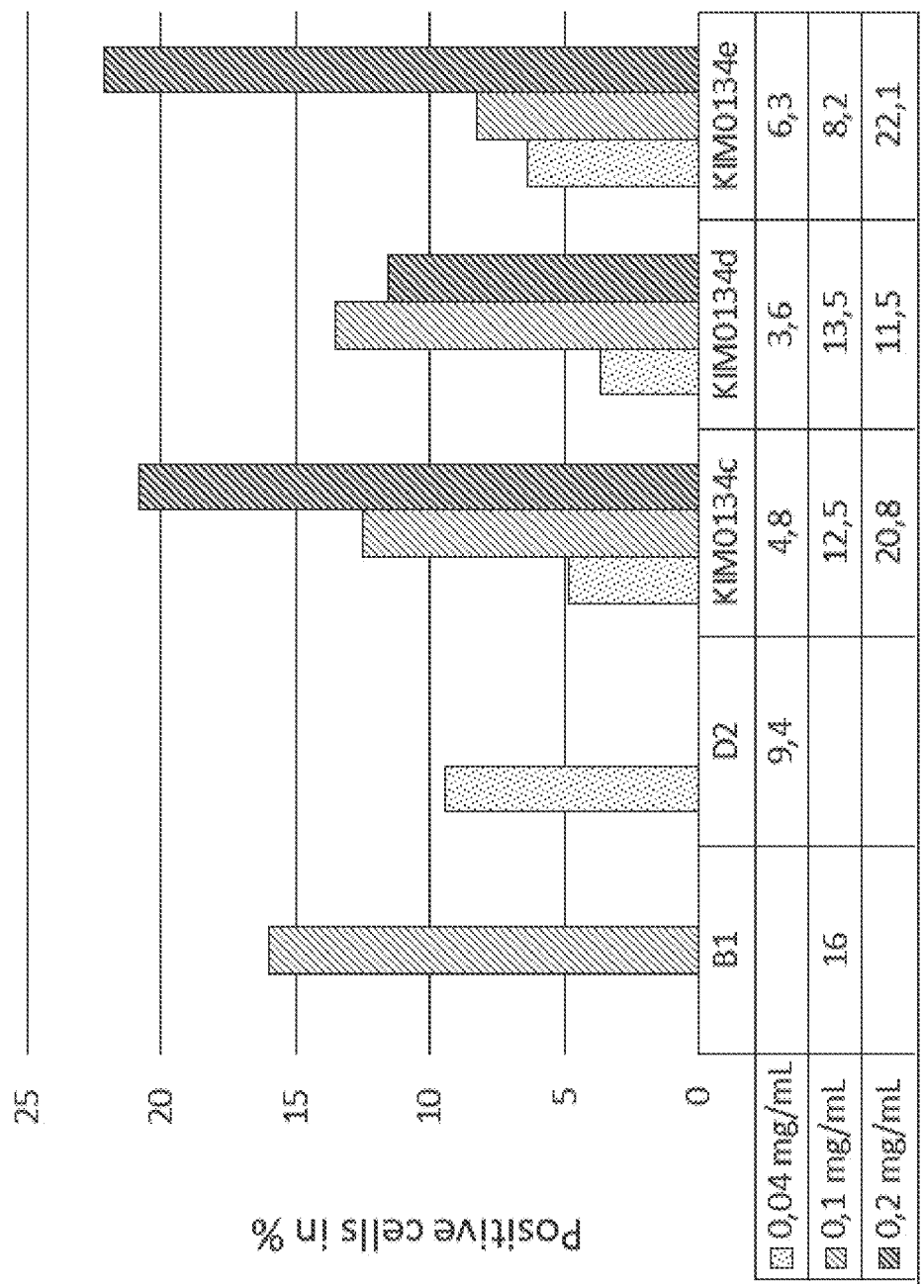
FIG. 20 shows a comparison of flow cytometry measurements obtained with human breast cancer cells (MCF-7) after labeling with different batches of double fluorescent particles (SA-MIP and SA-NIP).

FIG. 20 shows a comparison of flow cytometry measurements obtained with human breast cancer cells (MCF-7) after labeling with different batches of double fluorescent particles (SA-MIP and SA-NIP). Concentration of 0.1 mg/ml gave a higher % positive staining with KIM0134d (BAM SAMIPs) compared to KIM0134e (BAM SANIPs); 13.5% for BAM SAMIPs compared to 8.2% for BAM SANIPs. Here, the SA-MIPs are used, so SA is targeted. The stained breast cancer cells of cell line MCF-7 were analyzed by flow cytometry. Several different SAMIP batches are used. B1=MU SAMIPs of concentration 0.1 mg/ml; D2=BAM SAMIPs of 0.04 mg/ml (have been evaluated to give same results as MU SAMIP at 0.1 mg/l); and the batches KIM0134c, KIM0134d and KIM0134e. Looking at concentration 0.1 mg/ml, it can be seen that KIM0134d (SAMIPs) gives a higher staining result compared to KIM0134e (SANIPs).

Figure 21:
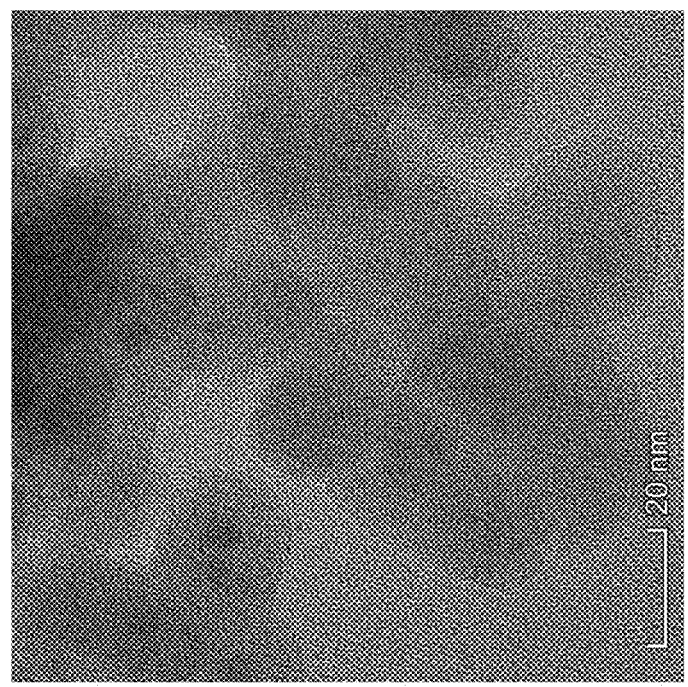
FIG. 21 shows schematically the generation of Eu(III)-doped or Tb(III)-doped silica particles and an exemplary TEM image of Tb(III)-doped SiO$_2$ particles according to example 3.
Figure 21:
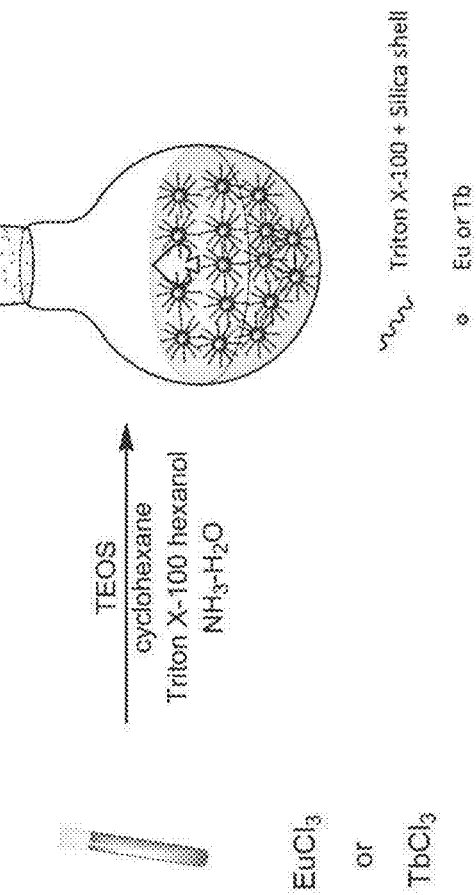

FIG. 21, left shows schematically the generation of Eu(III)-doped or Tb(III)-doped silica particles via a microemulsion method employing EuCl$_3$ or TbCl$_3$. An exemplary TEM image of Tb(III)-doped SiO$_2$ particles is shown on the right.

Figure 22:
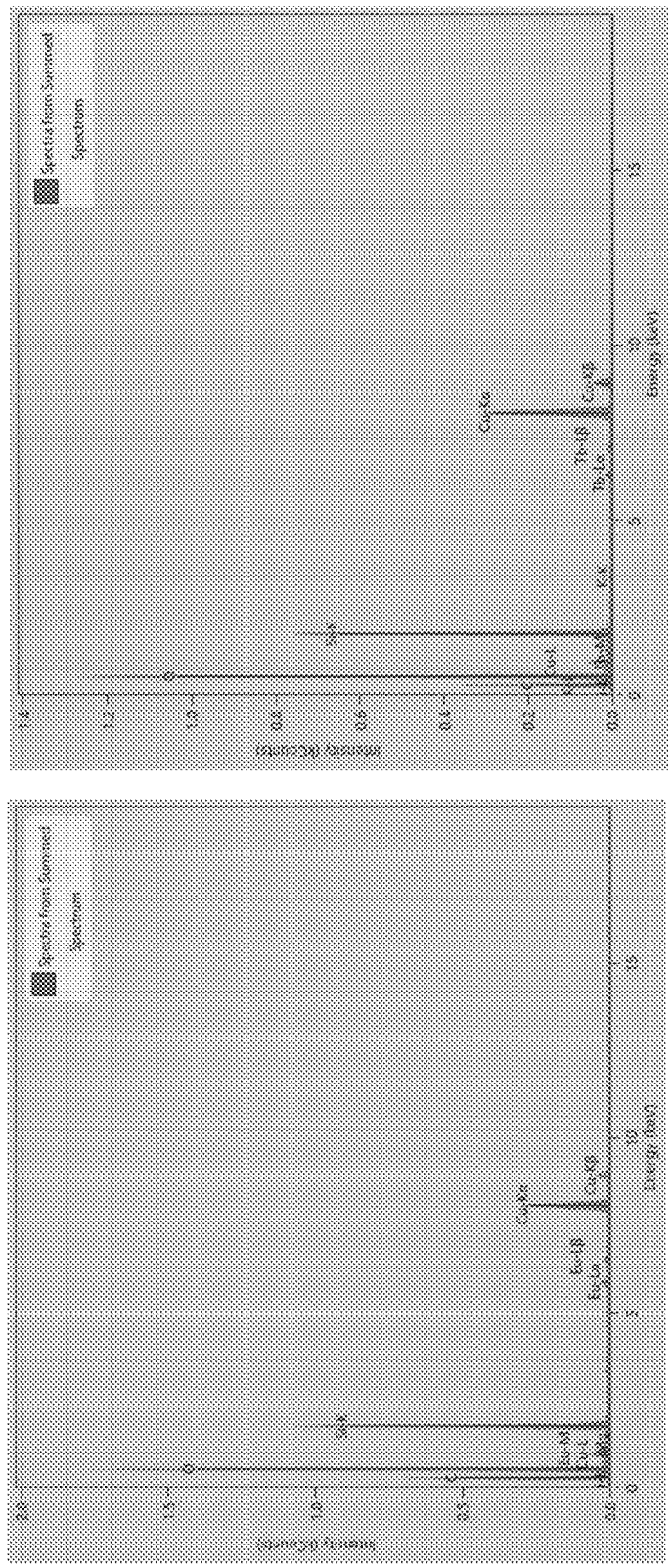
FIG. 22 shows two exemplary EDX spectra of Eu(III)-doped and Tb(III)-doped SiO$_2$ particles, respectively according to example 3.

FIG. 22 shows exemplary EDX spectra of Eu(III)-doped and Tb(III)-doped SiO$_2$ particles.

Figure 23:
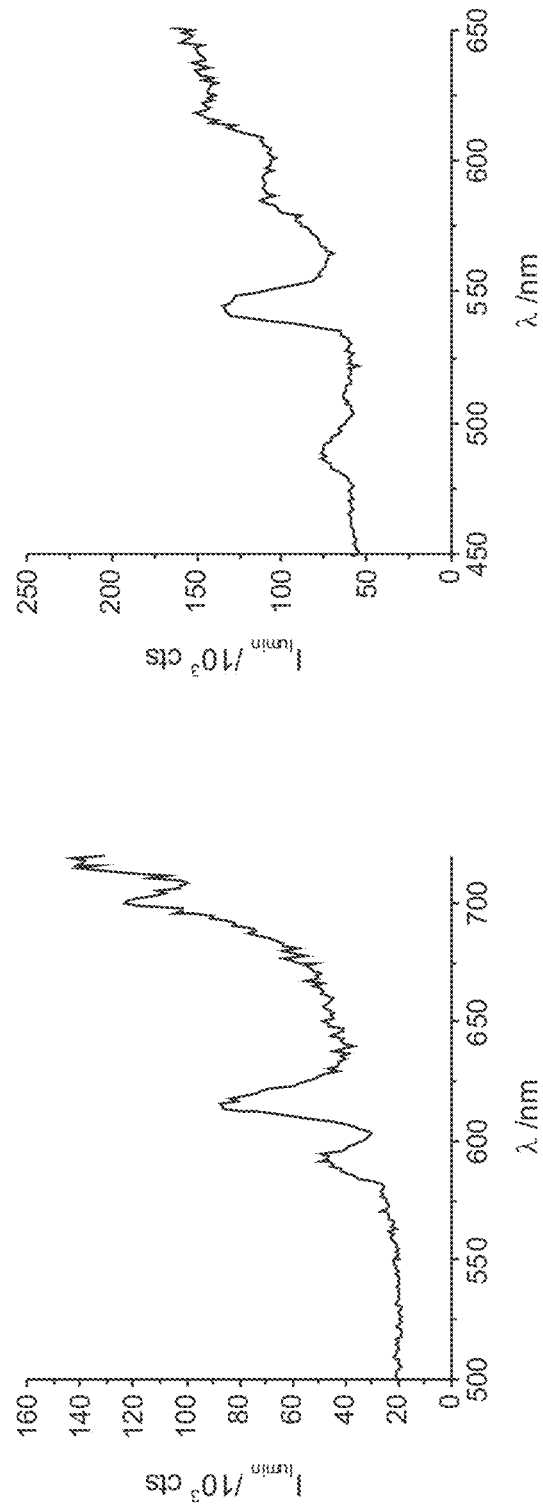
FIG. 23 shows exemplary luminescence spectra of Eu(III)-doped (left) and Tb(III)-doped SiO$_2$ particles (right) according to example 3.

FIG. 23 shows exemplary luminescence spectra of Eu(III)-doped and Tb(III)-doped SiO$_2$ particles suspended in water and excited at 375 nm.

Figure 24:
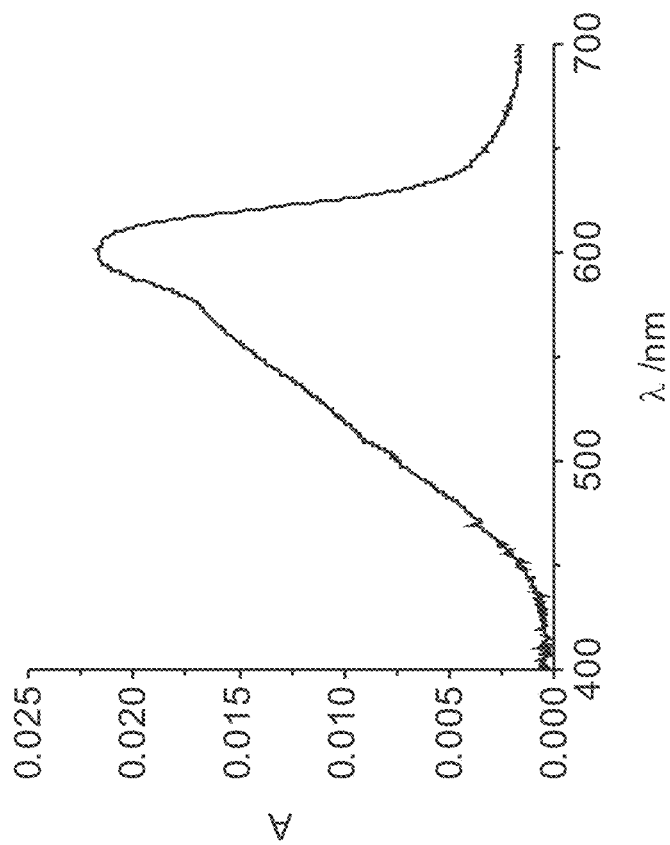
FIG. 24 shows exemplary TEM images of nile blue- (top) and cresyl violet-doped SiO$_2$ particles (bottom) and an exemplary absorption spectrum of cresyl violet-doped SiO$_2$ particles.
Figure 24:
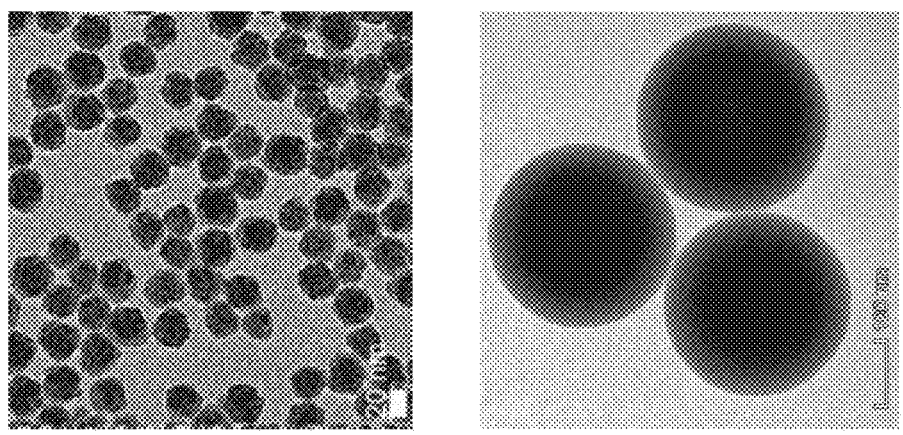

FIG. 24 shows exemplary TEM images of nile blue- (top left) and cresyl violet-doped (bottom left) SiO$_2$ particles and an exemplary absorption spectrum of cresyl violet-doped SiO$_2$ particles at 0.04 mg/mL in ethanol.

Figure 25:
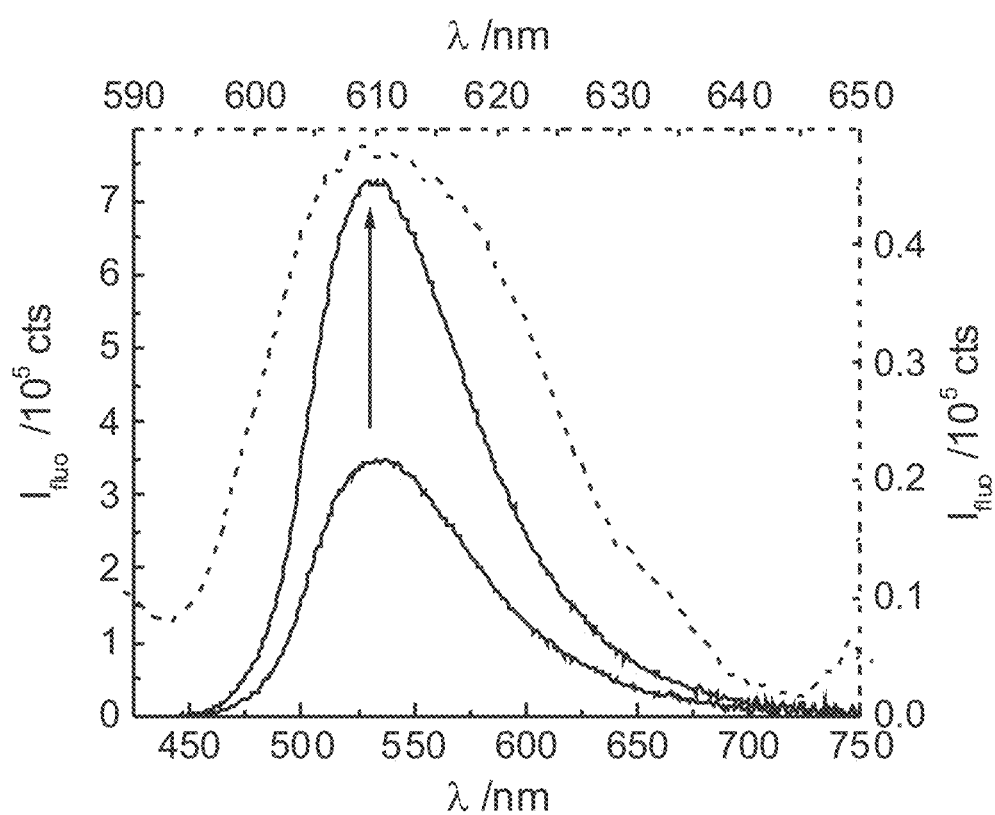
FIG. 25 shows the fluorescence emission spectra of the core domain (dashed) and the shell domain before and after the addition of sialic acid (solid) of dye-doped PS@SiO$_2$@MIP particles.

FIG. 25 shows the fluorescence emission spectra of the core domain (dashed) and the shell domain before and after the addition of sialic acid (solid) to dye-doped PS@SiO$_2$@MIP particles suspended at 0.2 mg/mL in dimethylformamide. Dye III (Emission maximum at 610 nm) is doped into the polymer core and its emission excited using light of wavelength 550 nm. Probe monomer I (Emission maximum at 530 nm) is covalently integrated into the MIP shell and excited at 404 nm. The emission of the MIP shell is recorded before and after addition of 60 µM sialic acid (analyte) in DMF; the arrow indicates the analyte-induced fluorescence increase.

The described embodiments have versatile application areas for the detection of different single cells and cell groups in the medical, biochemical, and food diagnostic industries. With the aim to demonstrate the feasibility of suggested embodiments, some examples describing the used laboratory methods and materials are given below.

PRACTICAL EXAMPLES

1 Example 1

Fluorescent Carbon Nanodot Core/Silica Structural Shell/Fluorescent MIP Shell Particles (CND@SiO$_2$@MIP)

1.1 Materials

Acetonitrile, toluene, chloroform (all anhydrous), all other solvents (UV/Vis grade), 4-cyano-4-(phenylcarbonothioylthio)pentanoic acid (CPBA), (3-aminopropyl)triethoxysilane (APTES), ethyleneglycol dimethacrylate (EGDMA), citric acid, Triton X-100, methacrylic acid-2-isocyanatoethylester, tetrabutylammonium hydroxide (TBA-OH) and ethylene diamine were purchased from Sigma Aldrich. Ethylchloroformate and butylhydroxytoluene (BHT) were from Fluka and tetraethylorthosilicate (TEOS) and ammonia from Merck. Vinylbenzene boronic acid, 4-chloro-7-nitrobenzo[c][1,2,5]oxadiazole (NBD-Cl) and n-hexanol were purchased from Alfa Aesar, 2,2'-azobis (2,4-dimethylvaleronitrile) (ABDV) from Wako. N-Acetyl-neuraminic acid (sialic acid, SA) was purchased from Carl Roth. Milli-Q water was obtained with a Milli-Q-water purification system (Millipore Synthesis A10).

1.2 Instruments $^1$H and $^{13}$C NMR spectra were recorded on Bruker AV-400 and AVANCE III 500 spectrometers, mass spectra were obtained on a Waters LCT Premier XE-TOF mass spectrometer, and TEM images were registered with a Talos™ F200S (200 kV) transmission electron microscope, FEI Co. Elemental analyses were determined by using a Euro EA-Elemental analyzer. UV/Vis absorption spectra were recorded on an Analytik Jena Specord 210 Plus spectrophotometer. Steady-state fluorescence measurements were carried out on a Horiba Jobin-Yvon FluoroMax-4P spectrofluorometer by using standard 10 mm path length quartz cuvettes.

1.3 Synthesis of Probe Monomer I

1.3.1 Synthesis of 4-Amino-7-nitrobenzo[c][1,2,5]oxadiazole

NBD-Cl (1 g, 5.01 mmol) was dissolved in 25 mL MeOH. After addition of 3 mL ammonia (32%), the mixture was further stirred for 2 h. The solvent was evaporated under reduced pressure and the residue was purified by column chromatography on silica gel with acetone-cyclohexane (3:1-1:1) to obtain the product in 0.54 g (60%) as a brown powder, mp. 272-273° C. $^1$H NMR (400 MHz, CDCl$_3$): δ=8.46 (2H, d, J 8.0), 6.41 (2H, d, J 8.0). Elemental analysis calculated (%) for $C_6H_4N_4O_3$: C, 40.01; H, 2.24; N, 31.10. found: C, 40.23; H, 2.22; N, 30.84.

1.3.2 Synthesis of (2-(3-(7-Nitrobenzo[c][1,2,5]oxadiazol-4-yl)ureido)ethyl methacrylate) (I)

4-Amino-7-nitrobenzo[c][1,2,5]oxadiazole (200 mg, 1.1 mmol) was dissolved in 10 mL dry THF. After the addition of 20 mg BHT (butylhydroxytoluene) as stabilizer, methacrylic acid-2-isocyanatoethylester (257 mg, 1.7 mmol) was added and the mixture was further stirred for 12 h. The mixture was purified on silica gel with acetone-cyclohexane (5:1-2:1) to yield 294.8 mg of a yellow powder of I (cf. Scheme 1 below). $^1$H NMR (400 MHz, CDCl$_3$): δ=8.49 (1H, d, J 8.5), 8.18 (1H, d, J 8.5), 8.13 (1H), 6.11 (1H, t), 5.65 (1H, t) 5.58 (1H, t), 4.32 (2H, t, J 5.0), 3.63 (2H, q, J 5.0), 1.90 (3H, s). $^{13}$C NMR (100 MHz, DMSO-d$_6$): δ=166.02, 153.20, 144.86, 142.94, 136.33, 135.28, 127.04, 125.61, 108.93, 62.98, 37.97, 17.51. Elemental analysis calcd (%) for $C_{13}H_{13}N_5O_6$: C, 46.57; H, 3.91; N, 20.89. found: C, 46.69; H, 3.89; N, 20.68; HRMS (ESI-): m/z [M-H]- calcd. for $C_{13}H_{13}N_5O_6$: 334.0793, found: 334.0790.

Scheme 1: Probe monomer I

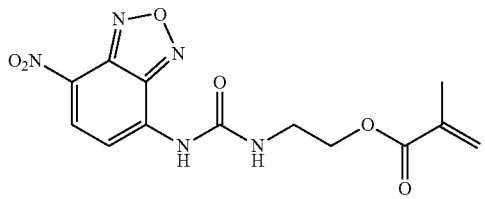 [SMILES: C=C(C)C(=O)OCCNC(=O)Nc1ccc([N+](=O)[O-])c2nonc12]

1.4 Synthesis of Carbon Nanodots (CND)

Citric acid (0.840 g) and ethylene diamine (1072 µL) were dissolved in Milli-Q water (20 mL). After transfer to a poly(tetrafluoroethylene) (Teflon)-lined autoclave (25 mL), the solution was heated at 200° C. for 5 h. After the reaction, the reactors were cooled to room temperature. The product, which was brown-black and transparent, was subjected to dialysis for 24 h to obtain the CNDs.

1.5 Silica Coating of Carbon Nanodot Core Particles (CND@SiO$_2$)

A water-in-oil (W/O) microemulsion was prepared by mixing 17.7 g Triton X-100, 77 mL cyclohexane, 16 mL n-hexanol, and 3.4 mL Milli-Q water in a 250 mL glass flask and stirring for 15 min. Then, 0.40 mL of an aqueous solution of CNDs (0.1 mL CNDs in 1 mL Milli-Q water at pH=2) were added to the emulsion and stirred for 5 min, followed by the addition of 0.50 mL TEOS and another 30 min of stirring. The hydrolysis of TEOS was initiated by adding 1.0 mL NH$_4$OH, and the mixture was stirred at room temperature for 24 h. After completion of silica coating, 50 mL ethanol were used to break the microemulsion. The silica-coated carbon nanodots (CND@SiO$_2$) were isolated after washing four times with ethanol and drying in a vacuum oven.

1.6 Modification with (3-Aminopropyl)triethoxysilane (CND@SiO$_2$-APT)

To a solution of 500 mg CND@SiO$_2$ in 60 mL dry toluene, 4 mL APTES were added. The mixture was degassed for 30 min while heating up to 120° C. under reflux. The reaction was kept stirring for 24 h under Ar atmosphere. After the reaction was complete, CND@SiO$_2$-APT were precipitated by adding 20 mL of cyclohexane and washed three times with toluene.

1.7 Modification with RAFT Agent (CND@SiO$_2$-RAFT)

To a solution of 190 mg CPBA in 10 mL dry THF, 65 µL ethylchloroformate and 94 µL triethylamine were added and the mixture was flushed with Ar while stirring. The mixture was kept at −78° C. for 40 min under Ar atmosphere. In the meantime, 0.8 g CND@SiO$_2$-APT were dissolved in 3.7 mL dry THF, flushed with Ar and kept at −10° C. Cooled CND@SiO$_2$-APT were added to the CPBA mixture under Ar atmosphere (using a syringe) and stirring was continued for 24 h at room temperature. The nanoparticles (CND@SiO$_2$-RAFT) were precipitated with 46 mL hexane and washed three times with acetone and two times with THF before drying in a vacuum oven overnight.

1.8 Preparation of MIP and NIP Shells on CND@SiO$_2$-RAFT (CND@SiO$_2$@MIP; CND@SiO$_2$@NIP)

To a solution of SA (1.325 mg) in 0.7 mL MeCN, 0.7 mL of a tetrabutylammonium hydroxide (TBA-OH) stock solution (4.90 mg TBA-OH·x30H$_2$O in 1.0 mL MeCN) were added and sonicated for 10 min. Then, 200 µL toluene were added into the SA-TBA mixture, followed by 30 min sonication and evaporation with a vacuum concentrator (30 min at 51 mbar, 1 h at 0 mbar) at room temperature (material A). To a solution of 21.44 µL of 2-aminoethyl methacrylate hydrochloride stock solution (10 mg 2-aminoethyl methacrylate hydrochloride in 40 µL Milli-Q water), 2.4 mg vinylbenzene boronic acid and 5.47 mg I in 8 mL MeOH and 122.88 µL EGDMA were added and sonicated for 15 min (solution B). For MIP coating, 0.5 mL as-prepared SA-TBA (material A, re-dissolved in 0.5 mL MeOH) were added to 2.5 mL of solution B in a glass vial. For NIP coating, only 0.5 mL MeOH were added to 2.5 mL of solution B in a second vial. Then, 2×150 mg CND@SiO$_2$-RAFT were added into the MIP and NIP vials and sonicated for 20 min. After degassing for 30 min, 0.6 mL ABDV solution (3.4 mg ABDV in 3 mL MeOH) were added to the MIP and NIP vials. Polymerization was triggered when the temperature reached 50° C. and stirring at 500 rpm was continued overnight. CND@SiO$_2$@MIP and CND@SiO$_2$@NIP were isolated after washing three times with 1.25 mL of a solution containing 80.9% methanol, 14.3% formic acid and 4.8% Milli-Q water) for one hour and drying in a vacuum oven overnight. Herein, the abbreviation "NIP" indicates non-imprinted polymer shells used as controls. Put differently, the synthesis is done in the same way as for the MIP only that the template is missing.

2 Example 2

Fluorescent Polystyrene Core/Silica Structural Shell/Fluorescent MIP Shell Particles (PSII@SiO₂@MIP)

2.1 Materials

All organic solvents were purchased from Th. Geyer and used without further purification unless otherwise indicated. Styrene, 2,2'-azobis(2-methylpropionamidine)dihydrochloride (AIBA), (3-aminopropyl)triethoxysilane (APTES), methacrylamide, ethylene glycol dimethacrylate (EGDMA), 4-cyano-4-(phenylcarbonothioylthio)pentanoic acid, anhydrous tetrahydrofuran (THF), dimethylformamide (DMF), tetraethylorthosilicate (TEOS), sodium dodecylbenzene sulphonate (SDS) and nitric acid were obtained from Sigma Aldrich. Triethylamine, formic acid and hydrochloric acid were obtained from Applichem. Basic alumina was purchased from Acros Organics, N-acetylneuraminic acid (sialic acid, SA) from Carl Roth and ethylchloroformate from Fluka. 2,2'-Azobis(2,4-dimethylvaleronitril) (ABDV) initiator was obtained from Wako Chemicals. L-Lysine was purchased from J&K Chemicals and vinylbenzene boronic acid from ThermoFischer. Probe monomer I (2-(3-(7-nitrobenzo[c][1,2,5]oxadiazol-4-yl)ureido)ethyl methacrylate) was synthesized as described in Section 1.1.3; dye II ((E)-7-(4-(dimethylamino)styryl)-5,5-difluoro-10-(8-hydroxyquinolin-2-yl)-1,3,9-trimethyl-5H-dipyrrolo[1,2-c:1', 2'-f][1,3,2]diazaborinin-4-ium-5-uide) was synthesized according to Y.-H. Yu, A. B. Descalzo, et al., Chem. Asian J. 2006, 1, 176; dye III (7,7-difluoro-5,9-dimethyl-14-phenyl-7H-[1,3,2]diazaborinino[4,3-a:6,1-a']diisoindol-6-ium-7-uide) was synthesized according to A. B. Descalzo, H.-J. Xu et al., Org. Lett. 2008, 10, 1581. Milli-Q water was from a Milli-Q ultrapure water purification system (Millipore Synthesis A10).

2.2 Instruments

TEM measurements were carried out on a FEI Talos™ F200S (200 kV) scanning/transmission electron microscope. Fluorescence spectra were recorded on a Horiba Jobin-Yvon FluoroMax-4P spectrofluorometer with standard 10 mm path length quartz cuvettes.

2.3 Synthesis of Polystyrene Core Particles (PS)

Inhibitor was removed from styrene by passing through a basic alumina column. 8.96 mL Milli-Q water was added to a screw capped glass vial with a septum and the solution was stirred for 10 min at 75° C. at 600 rpm while degassing with Argon. 0.05 mL inhibitor-free styrene was added to the glass vial using a syringe under Argon atmosphere and mixing was continued for further 10 min. Meanwhile, 6.3 mg AIBA were dissolved in 1.575 mL Milli-Q water and degassed for 10 min with Argon, after which 1 mL was added to the water-styrene mixture using a syringe. The reaction mixture was left for 5 h, and thereafter cooled to room temperature. The particles were precipitated with a 0.1% aqueous solution of SDS, cleaned three times with Milli-Q water, and dried in a vacuum.

2.4 Dye-Doping of Polystyrene Core Particles (PSII)

500 mg of PS particles were dispersed in 10 mL Milli-Q water in a glass vial using an ultrasonic bath (freq. 37 Hz, power 100%). 1300 µL of the stock solution were pipetted into several 2 mL plastic vials placed in a holder. Several concentrations (millimolar range) of doping solution were prepared in THF, by dissolving the respective amounts of dye II (cf. Scheme 2 below). For each vial containing a polystyrene suspension, 130 µL of dye solution were added, and the same volume of THF was added for the blank. Immediately after addition of dye solution/THF, the particle suspensions were vortexed briefly, covered with foil then placed on a rotation plate for 30 min at 40 rpm. Afterwards, the particles were centrifuged at 10,000 rpm for 5 min, washed two times with 1600 µL of Milli-Q water and once with 1600 µL of EtOH (70%). Following all washes, the supernatant was carefully removed. The particles were then dried in a vacuum at room temperature.

Scheme 2: Dye II used for doping

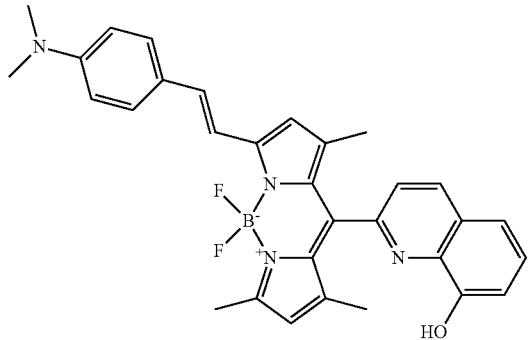

2.5 Silica Coating of Dye-Doped Polystyrene Core Particles (PSII@SiO₂)

1 mL of a 0.05% PSII suspension in Milli-Q water was further diluted with 1.9 mL Milli-Q water in a 2 mL plastic vial. 10 µL 1 M HNO₃ were added to obtain a pH=3, which was confirmed with pH indicator paper. The dispersion was mixed for 15 min at 700 rpm at 60° C., after which 2.8 mg L-Lysine and 9 µL TEOS were added. The mixture was covered with foil and left to react for 6 h. The resultant particles were cleaned three times in a water/ethanol mixture and dried in a vacuum at room temperature.

2.6 Modification with (3-Aminopropyl)triethoxysilane (PSII@SiO₂-APT)

100 mg of PSII@SiO₂ were dispersed in 4 mL of absolute ethanol, and 2 mL of 9:1 Milli-Q:HCl were added. The mixture was sonicated for 10 min and centrifuged at 8700 rpm for 10 min. The particles were cleaned two times with ethanol, and re-dispersed in 2 mL ethanol. 100 µL of APTES were added, and the reaction allowed to proceed at 40° C. at 700 rpm for 24 h. The particles were washed three times in ethanol, and dried for 4 hours under vacuum at room temperature. A ninhydrin test after successful functionalization with APTES yielded an amino group density of 1.2 mmol g$^{-1}$.

2.7 Modification with RAFT Agent (PSII@SiO$_2$-RAFT)

0.428 mmol RAFT agent 4-cyano-4-(phenylcarbonothioylthio)pentanoic acid, 0.428 mmol ethylchloroformate and 0.428 mmol triethyl amine were dissolved in 10 mL anhydrous THF and kept at −78° C. in a liquid nitrogen/acetone bath for 40 minutes. Simultaneously, 100 mg of PSII@SiO$_2$-APT were kept in an ice bath at −10° C. Afterwards, the THF solution was added to the particles and the mixture stirred at ambient temperature overnight at 700 rpm. The particles were precipitated in 60 mL hexane, washed two times in THF, and dried in a vacuum.

2.8 Preparation of MIP and NIP Shells on PSII@SiO$_2$-RAFT (PSII@SiO$_2$@SAMIP; PSII@SiO$_2$@NIP)

5.1383 mg Methacrylamide were dissolved in 40 μL DMF (solution A). 2.4 mg Vinylbenzeneboronic acid, 5.47 mg of probe monomer I (FIG. 1), 21.44 μL of solution A, 122.88 μL EGDMA and 8 mL DMF were mixed and sonicated for 15 min in an ultrasonic bath (solution B). Solution B was split into 2×2.5 mL in 4 mL brown glass vials; 0.5 mL DMF (solution C1—NIP) was added to one vial and 0.5 mL SA stock solution (solution C2—SA-MIP) to another vial. The SA stock solution was prepared by dissolving 1.325 mg SA in 0.5 mL DMF with sonication. 2×50 mg of PSII@SiO$_2$-RAFT were weighed into separate 4 mL brown glass vials. 2.54 mL of solution C1 was added to one vial (NIP) and 2.54 mL of solution C2 to another vial (SAMIP). All suspensions were dispersed in an ultrasonic bath for 20 min with shaking in between to form a suspension. In the meantime, 3.4 mg ABDV were dissolved in 3 mL DMF and degassed with Argon till usage. The SAMIP and NIP suspensions were degassed for 20 min with Argon, and afterwards, 0.6 mL of ABDV solution was added to each vial under inert gas atmosphere. The samples were left to stir for 22 h at 500 rpm at 50° C. The resultant particles were centrifuged for 1 min at 6000 rpm, then washed with 1.25 mL of a solution of 80.9% Methanol, 14.3% formic acid and 4.8% Milli-Q water. The suspension was left in the thermomixer for 1 h at 25° C. and 1000 rpm, and the particles were centrifuged thereafter for 1 min at 6000 rpm. The washing was repeated four times. Afterwards, 3.75 mL methanol was added and the suspensions left for 30 min in the rotator at 40 rpm at room temperature. The particles were centrifuged for 1 min at 6000 rpm, and dried in a vacuum.

2.9 Choice of Dye for Doping

For doping as described in item 2.4, dye III (cf. Scheme 3) can be alternatively used.

Scheme 3: Dye III used for doping

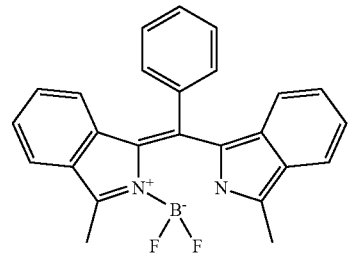

3 Example 3

Luminescent Silica Core/Fluorescent MIP Shell Particles (LnSiO$_2$@MIP)

3.1 Materials

Acetonitrile, toluene, chloroform (all anhydrous), all other solvents (UV/Vis grade), 4-cyano-4-(phenylcarbonothioylthio)pentanoic acid (CPBA), (3-aminopropyl)triethoxysilane (APTES), ethyleneglycol dimethacrylate (EGDMA), EuCl$_3$ (anhydrous, powder, 99.99% trace metals basis), TCl$_3$ (anhydrous, powder, 99.99% trace metals basis), Triton X-100, methacrylic acid-2-isocyanatoethylester and tetrabutylammonium hydroxide (TBA-OH) were purchased from Sigma Aldrich. Ethylchloroformate and butylhydroxytoluene (BHT) were from Fluka and tetraethylorthosilicate (TEOS) and ammonia from Merck. Vinylbenzene boronic acid, 4-chloro-7-nitrobenzo[c][1,2,5]oxadiazole (NBD-Cl) and n-hexanol were purchased from Alfa Aesar, 2,2'-azobis(2,4-dimethylvaleronitrile) (ABDV) from Wako. N-Acetylneuraminic acid (sialic acid, SA) was purchased from Carl Roth. Milli-Q water was obtained with a Milli-Q-water purification system (Millipore Synthesis A10).

3.2 Instruments

TEM measurements were carried out on a FEI Talos™ F200S (200 kV) scanning/transmission electron microscope. Fluorescence spectra were recorded on a Horiba Jobin-Yvon FluoroMax-4P spectrofluorometer with standard 10 mm path length quartz cuvettes.

3.3 Synthesis of Lanthanide-Ion-Doped Silica Core Particles (LnSiO$_2$)

A water-in-oil (W/O) microemulsion was prepared by mixing 17.7 g Triton X-100, 77 mL cyclohexane, 16 mL n-hexanol, and 3.4 mL Milli-Q water in a 250 mL glass flask and stirring for 15 min. Then, 0.40 mL of an aqueous solution of LnCl$_3$ (775 mg EuCl$_3$ or 796 mg TbCl$_3$ in 1 mL Milli-Q water at pH=2) were added to the emulsion and stirred for 5 min, followed by the addition of 0.50 mL TEOS and another 30 min of stirring. The hydrolysis of TEOS was initiated by adding 1.0 mL NH$_4$OH, and the mixture was stirred at room temperature for 24 h. After completion of silica coating, 50 mL ethanol were used to break the microemulsion. The silica-coated LnCl$_3$ (LnSiO$_2$) were isolated after washing four times with ethanol and drying in a vacuum oven.

3.4 Modification with (3-Aminopropyl)triethoxysilane (LnSiO$_2$-APT)

To a solution of 400 mg LnSiO$_2$ in 60 mL dry toluene, 4 mL APTES were added. The mixture was degassed for 30 min while heating up to 120° C. under reflux. The reaction was kept stirring for 24 h under Ar atmosphere. After the reaction was complete, LnSiO$_2$-APT were precipitated by adding 20 mL of cyclohexane and washed three times with toluene.

3.5 Modification with RAFT Agent (LnSiO$_2$-RAFT)

To a solution of 190 mg CPBA in 10 mL dry THF, 65 µL ethylchloroformate and 94 µL triethylamine were added and the mixture was flushed with Ar while stirring. The mixture was kept at −78° C. for 40 min under Ar atmosphere. In the meantime, 0.7 g LnSiO$_2$-APT were dissolved in 3.7 mL dry THF, flushed with Ar and kept at −10° C. Cooled LnSiO$_2$-APT were added to the CPBA mixture under Ar atmosphere (using a syringe) and stirring was continued for 24 h at room temperature. The nanoparticles (LnSiO$_2$-RAFT) were precipitated with 46 mL hexane and washed three times with acetone and two times with THF before drying in a vacuum oven overnight.

3.6 Preparation of MIP and NIP Shells on LnSiO$_2$-RAFT (LnSiO$_2$@MIP; LnSiO$_2$@NIP)

To a solution of SA (1.325 mg) in 0.7 mL MeCN, 0.7 mL of a tetrabutylammonium hydroxide (TBA-OH) stock solution (4.90 mg TBA-OH·×30H$_2$O in 1.0 mL MeCN) were added and sonicated for 10 min. Then, 200 µL toluene were added into the SA-TBA mixture, followed by 30 min sonication and evaporation with a vacuum concentrator (30 min at 51 mbar, 1 h at 0 mbar) at room temperature (material A). To a solution of 21.44 µL of 2-aminoethyl methacrylate hydrochloride stock solution (10 mg 2-aminoethyl methacrylate hydrochloride in 40 µL Milli-Q water), 2.4 mg vinylbenzene boronic acid and 5.47 mg I in 8 mL MeOH and 122.88 µL EGDMA were added and sonicated for 15 min (solution B). For MIP coating, 0.5 mL as-prepared SA-TBA (material A, re-dissolved in 0.5 mL MeOH) were added to 2.5 mL of solution B in a glass vial. For NIP coating, only 0.5 mL MeOH were added to 2.5 mL of solution B in a second vial. Then, 2×130 mg LnSiO$_2$-RAFT were added into the MIP and NIP vials and sonicated for 20 min. After degassing for 30 min, 0.6 mL ABDV solution (3.4 mg ABDV in 3 mL MeOH) were added to the MIP and NIP vials. Polymerization was triggered when the temperature reached 50° C. and stirring at 500 rpm was continued overnight. LnSiO$_2$@MIP and LnSiO$_2$@NIP were isolated after washing three times with 1.25 mL of a solution containing 80.9% methanol, 14.3% formic acid and 4.8% Milli-Q water) for one hour and drying in a vacuum oven overnight. Herein, as before, the abbreviation "NIP" indicates non-imprinted polymer shells used as controls. Put differently, the synthesis is done in the same way as for the MIP only that the template is missing.

4 Example 4

Fluorescent Silica Core/Fluorescent MIP Shell Particles (DySiO$_2$@MIP)

4.1 Materials

All organic solvents were purchased from Th. Geyer and used without further purification unless otherwise indicated. Cresyl violet perchlorate, (3-aminopropyl)triethoxysilane (APTES), methacrylamide, ethylene glycol dimethacrylate (EGDMA), 4-cyano-4-(phenylcarbonothioylthio)pentanoic acid, anhydrous tetrahydrofuran (THF), dimethylformamide (DMF), tetraethylorthosilicate (TEOS) and nitric acid were obtained from Sigma Aldrich. Triethylamine and formic acid were obtained from Applichem. Basic alumina was purchased from Acros Organics, N-acetylneuraminic acid (sialic acid, SA) from Carl Roth and ethylchloroformate from Fluka. 2,2'-Azobis(2,4-dimethylvaleronitril) (ABDV) initiator was obtained from Wako Chemicals. Vinylbenzene boronic acid was obtained from ThermoFischer. Probe monomer I (2-(3-(7-nitrobenzo[c][1,2,5]oxadiazol-4-yl)ureido)ethyl methacrylate) was synthesized as described in Section 1.1.3. Probe monomer I (2-(3-(7-nitrobenzo[c][1,2,5]oxadiazol-4-yl)ureido)ethyl methacrylate) was synthesized as described in Section 1.1.3; Milli-Q water was from a Milli-Q ultrapure water purification system (Millipore Synthesis A10).

4.2 Instruments

TEM measurements were carried out on a FEI Talos™ F200S (200 kV) scanning/transmission electron microscope. Fluorescence spectra were recorded on a Horiba Jobin-Yvon FluoroMax-4P spectrofluorometer with standard 10 mm path length quartz cuvettes.

4.3 Synthesis of Dye-Doped Silica Core Particles (DySiO$_2$)

1 mg cresyl violet perchlorate and 9.1 mg L-arginine were dissolved in 6.9 ml water while thoroughly mixing the solution in a 20 mL vial. Then 0.45 ml cyclohexane was added to the water-arginine solution and the reaction was heated to 60° C. in a water bath under stirring at 300 rpm. Once the reactants warmed up, 0.55 ml TEOS were added and after 20 h the particles were washed 3× with ethanol and dried in the vacuum oven. The resulting dye-doped silica, i.e. dye-doped silica nanoparticles can be used as a core of the suggested double fluorescent particles and generate their first fluorescence.

4.4 Modification with (3-Aminopropyl)triethoxysilane (DySiO$_2$-APT)

1 g of the silica particles was dispersed in 40 mL toluene and heated to 120° C. 4 mL of APTES was added and the reaction was continued for 24 hours. The particles were then washed 1× with toluene, 2× in water and 2× in ethanol 96%. Afterwards the particles were dried in the vacuum oven.

4.5 Modification with RAFT Agent (DySiO$_2$-RAFT)

0.428 mmol 4-Cyano-4-(phenylcarbonothioylthio)pentanoic acid, 0.428 mmol ethylchloroformate and 0.428 mmol triethyl amine were dissolved in 10 mL anhydrous THF and kept at −78° C. in a liquid nitrogen/acetone bath for 40 minutes. Simultaneously, 100 mg of the APTES modified particles were kept in an ice bath at −10° C. Afterwards, the THF solution was added to the particles and the mixture stirred at ambient temperature overnight at 700 rpm. The particles were precipitated in 60 mL hexane, washed two times in THF, and dried under vacuum.

4.6 Preparation of MIP and NIP Shells on DySiO$_2$-RAFT (DySiO$_2$@SAMIP; DySiO$_2$@NIP)

1.325 mg SA was dissolved in 0.5 mL DMF with sonication. 5.1383 mg methacrylamide were dissolved in 40 µL DMF (solution A). 2.4 mg vinylbenzeneboronic acid, 5.47 mg of dye monomer I, 21.44 µL of solution A, 122.88 µL EGDMA and 8 mL DMF were mixed and sonicated for 15 m in an ultrasonic bath (solution B). Solution B was split into 2×2.5 mL in 4 mL brown glass vials; 0.5 mL DMF (Stock solution B1—NIP) was added to 1 vial and 0.5 mL SA stock solution (Stock solution B2—SA-MIP) to another vial. 2×50 mg of the RAFT modified, dye-doped particles were weighed into separate 4 mL brown glass vials. 2.54 mL of solution B1 was added to one vial (NIP) and 2.54 mL of solution B2 to another vial (SA-MIP). All suspensions were dispersed in the US bath for 20 min with shaking in between to form a suspension. In the meantime, 3.4 mg ABDV were dissolved in 3 mL DMF and degassed with Argon till usage. The MIP and NIP suspensions were degassed for 20 min with Argon, and afterwards 0.6 mL of ABDV solution was added to each vial under inert gas atmosphere. The samples were left to stir for 22 h at 500 rpm at 50° C. The resultant particles were centrifuged for 1 min at 6000 rpm, then washed with 1.25 mL of a solution of 80.9% Methanol, 14.3% formic acid and 4.8% Millipore water. The suspension was left in the thermomixer for 1 h at 25° C. and 1000 rpm, and particles centrifuged thereafter for 1 min at 6000 rpm. The washing was repeated 4 times. Afterwards, 3.75 mL methanol was added and the suspensions left for 30 min in the rotator at 40 rpm and room temperature. The particles were centrifuged for 1 min at 6000 rpm, and dried under vacuum.

4.7 Characterization of Particles

4.7.1 TEM Measurements 1 mg mL$^{-1}$ Suspensions of PSII@SiO$_2$@SAMIP and PSII@SiO$_2$@NIP were prepared, and 2 µL placed on a grid for TEM measurements. Images were analysed with Image J software.

4.7.2 Fluorescence Titrations 0.05 mg mL$^{-1}$ Suspensions of the dye-doped particles were prepared in Milli-Q water and the fluorescence spectra measured. 0.25 mg mL$^{-1}$ Suspensions of the MIP and NIP particles were prepared in DMF; a 1 mM solution of SA in DMF was also prepared. Increasing volumes of the 1 mM SA solution were added to 2 mL suspensions of the MIP and NIP particles, and the resultant fluorescence spectra were recorded $$\frac{\Delta F}{F_0} = \frac{F_x - F_0}{F_0}$$

was calculated for each fluorescence spectrum of the MIP and NIP (where $F_x$ is the maximum fluorescence intensity for each spectrum after SA addition, while $F_o$ is the maximum fluorescence intensity before addition of SA). The imprinting factor was determined from the MIP:NIP ratio of $$\frac{\Delta F}{F_0}$$

at the saturation point of the titration.

5 Cell Staining Protocols

Fluorescent Polystyrene Core/Silica Structural Shell/Fluorescent MIP Shell Particles (PSII@SiO$_2$@MIP)

5.1 Staining in Phosphate Buffered Saline (PBS)

In the following, a brief description of process steps used for cell labelling (also designated as staining) in PBS is given:

Firstly, the culture medium (from T75 flask) was removed and the cells were rinsed (with 5 mL) PBS without Ca/Mg. Then, 500 µL trypsin/EDTA was used to cover the cells in a T75 flask. The cells were incubated for 5-10 min at 37° C. Subsequently, 5 mL of medium were added and the cell suspension was aspirated a few times in the pipette to loosen any remaining bonds and cells attached. A hemocytometer (Bürker cell counting chamber) was used to count the cells stained with Trypan Blue (50 µL cells+50 µL Trypan Blue). 3×10$^6$ of the cells were transferred to a 15 mL tube and centrifuged for 5 min at 300×g. The supernatant was removed and cell pellets were washed twice with 2 mL PBS. Then, the cells were divided in FACs tubes (1×10$^6$ cells each sample) and all the supernatant was removed by centrifuge for 5 min at 300×g. Finally, the cells were stained with 100 µL of each MIP particle concentration under investigation and incubated for 60 min at 4° C. (one ice). Following steps comprise: Adding unstained 100 µL PBS; 0.1 mg mL$^{-1}$ MIP particles (stock solution 1 mg mL$^{-1}$): 10 µL MIP particles+90 µL PBS; 0.2 mg mL$^{-1}$ MIP particles (stock solution 1 mg mL$^{-1}$): 20 µL MIP particles+80 µL PBS; Washing of the cells with 3×2 mL PBS.

For flow cytometry analysis, the pellets were resuspended in 300 µL PBS and analysed by flow cytometry (e.g., on a BD Accuri C6 Flow Cytometer, BD, NJ, USA).

For fluorescence or digital holographic microscopy analysis the cells were fixed by adding 1 mL 4% formaldehyde in PBS and incubated for 10 min at room temperature. Afterwards the cells were washed 3× with 2 mL PBS. Finally the pellets were resuspended in 10-20 µL PBS and 10 µL of the cells were added in Bürker chamber and analysed by microscopy.

5.2 Staining in Methanol:Water

In the following, a brief description of process steps used for cell labelling (also designated as staining) in MeOH:H$_2$O is given:

Firstly, the dried polymer particles are resuspended in methanol:water (1:30, v/v). A stock solution of 0.8 mg mL$^{-1}$ was prepared by sonication for 4+4 minutes with an ultrasonic bath, e.g. a VWR ultrasonic cleaner. Human prostate cancer cell lines, DU145 and PC-3 (LGC Standards, Teddington, Middlesex, UK), were cultured in flasks with Dulbecco's Modified Eagle Medium (DMEM) with 10% FBS and incubated at 37° C. with 5% CO$_2$ in 100% humidity. Cells were passaged by washing with PBS and then treated with trypsin/EDTA, when they reached confluency.

For microscopy studies, the cells were cultured in 12-well cell culture plates equipped with round glass cover slips (diameter 12 mm). 10,000 DU145 cells and 20,000 PC-3 cells, respectively, were prepared in 100 µL of cell suspension and pipetted onto each cover slip. After 3 h, 1 mL of cell culture medium was added and the cells were left to grow to reach confluency for at least 48 hours in 37° C. with 5% $CO_2$ in 100% humidity.

Each cover slip with confluent DU145 cells or PC-3 cells was washed twice with 2 mL PBS and fixed at room temperature for 10 min in 1 mL 4% formaldehyde. To stop fixation, the formaldehyde was aspirated from each well and washed 3× with 2 mL PBS.

For treatment with sialidase (neuraminidase from *Clostridium perfringens*, Sigma-Aldrich, St. Louis, MO, USA), the DU145 cells were washed with DMEM and 200 µL of 5 and 10 U $mL^{-1}$ of the enzyme, respectively, was added to the cells for 60 min in 37° C. One negative control was left with 200 µL of DMEM only. Thereafter, the cells were washed 3× with DMEM. Afterwards, the cells were washed twice with 2 mL methanol:water (1:30, vol/vol) and stained with MIP particles at a concentration of 20 µg $mL^{-1}$.

For fluorescence or digital holographic microscopy analysis: the cells were first washed twice with 2 mL methanol:water (1:30) for MIP particle staining. Thereafter, 500 µL of a sonicated MIP suspension of concentrations 80 µg $mL^{-1}$ or 20 µg $mL^{-1}$ were added to the wells, respectively, and one negative control left with 500 µL of methanol:water (1:30) only. The cells were incubated with MIPs for 60 min in 37° C. After incubation, the wells were washed 3× with 2 mL methanol:water (1:30, v/v) and each round glass cover slip was mounted for fluorescence microscopy imaging on a microscopy slide (upside down) with one drop of mounting medium Prolong® Gold antifade reagent with DAPI (Molecular Probes, USA).

For flow cytometry analysis, $5 \times 10^5$ cells of DU145 and PC3 were washed twice with 2 mL PBS and fixed at RT for 20 min in 1 mL 4% formaldehyde. Thereafter, the formaldehyde was aspirated from the cells and washed twice with 2 mL PBS. Afterwards, the cells were washed twice with 2 mL methanol/water (1:30) and stained with 500 µL sonicated MIP particles at different concentrations (2.5, 5 and 10 µg $mL^{-1}$) and incubated for 37° C. in 60 min. After incubation, the cells were washed twice with 2 mL methanol:water (1:30) and resuspended in 300 µL methanol:water and analysed with a flow cytometer (Accuri C6 Flow Cytometer, BD, NJ, USA).

6 Cell Viability of Cultured Cell Lines Incubated with MIP Particles $4 \times 10^4$ cells in 80 µL medium and 20 µL 1 mg $mL^{-1}$, 0.8 mg $mL^{-1}$, 0.4 mg $mL^{-1}$ or 0.2 mg $mL^{-1}$ of MIP particles in medium were incubated in 96-well plates for 24 h, 48 h and 73 h in triplicates along with a reference containing $4 \times 10^4$ cells in 100 µL medium and a control with 100 µL pure medium.

After incubation 20 µL CellTiter 96 Aqueous One Solution Cell Proliferation Assay (Promega, Madison, USA) was added and the samples were incubated for another 2 h. Afterwards, the absorbance at 490 nm was measured by using PowerWave XS (Bio-tex, USA).

Some aspects of the embodiments described herein can be summarized as follows.

1. Suggested is a fluorescent core-fluorescent MIP shell nano-object;
2. Suggested is a fluorescent core-structural shell-fluorescent MIP shell nano-object;
3. Suggested is a MIP-type probe adapted for ratiometric signal measurement;
4. Suggested are a dual-signaling probes adapted to cell surface binding and staining (labeling);
5. Suggested is using the above dual-signaling probes for microscopy
6. Suggested is using the dual-signaling probes for cytometry, especially for flow-cytometry;
7. Suggested is adapting the dual-signaling probes for cellular uptake;
8. Suggested is adapting the dual-signaling probes for a combination of cell surface binding, cell staining (labeling), and cellular uptake.

To summarize, the suggested embodiments offer the following advantages over previously known particles, preparation methods and methods of use. Particular advancements with respect to current microscopy/cytometry refer to the use of two different fluorescent reporter units which allow for ratiometric measurement and thus provide an intrinsic calibration against such variations as, e.g., light intensity (lamp performance). In contrast thereto, particles as described by Stsiapura et al. (2004), Holzapfel et al. (2005), and Long et al. (2010) offer merely one single fluorescence and thus heavily depend on a valid calibration under the current measurement conditions.

Further, the suggested MIP coated core-shell-nanoparticles provide enhanced stability and shelf-life of the MIPs compared to antibodies as recognition elements used, e.g., by Stsiapura et al. (2004), and Long et al. (2010). In contrast to Mao et al. (2012) and Demir et al. (2018) fluorescent monomers in a MIP are used. They allow for direct signaling and inherent calibration. Nanoparticle platforms guarantee small enough probes for labeling of live cells, wherein the MIP layer is thin enough to generate a sizeable signal change in contrast to Amjadi and Jalili (2017).

Furthermore, molecularly imprinted (mesoporous) silicas (MIS) as described by Amjadi and Jalili (2018), are less suited for the integration of dedicated fluorescent indicators or probes into the MIP shell, i.e. MIS-shell. Molecularly imprinted silicas are prepared from silane precursors, usually TEOS or TMOS (tetraethylorthosilicate or tetramethylorthosilicate) in a sol-gel type reaction. During silica network formation, the alkoxy groups of the precursors condense, liberating water and creating free silanol (Si—OH) groups. These hydroxy species would potentially interact in an unwanted way with most of the possible fluorescent monomers and compete with the designated template molecule for the binding sites. Directed imprinting for a defined spectroscopic response is thus not possible in a controlled fashion.

All MIS up to now thus rely on fluorescence quenching: the template/analyte bound somewhere close to the fluorescent unit in the MIS matrix can interact with the fluorophore and quench it. Specificity is thus essentially connected to the selectivity of the binding cavities; e.g., any smaller species which can enter the cavity and potentially interact with the fluorophore through these rather long-range forces can lead to quenching. Accordingly, for many of such systems the non-specific signals (false positives) are comparatively high.

As described, a typical double fluorescent particle comprises: a core with a first fluorescence; and a molecularly imprinted polymer (MIP) shell with a second fluorescence; wherein the MIP is an organic polymer comprising elements selected from the group consisting of: C, H, O, N, P, and S; wherein the MIP is adapted to selectively bind to a cell surface structure; wherein the first fluorescence is generated by an entity selected from the group consisting of: a carbon nanodot, a dye-doped polymer, a dye-doped stabilized micelle, a P-dot (a π-conjugated polymer), a quantum dot doped polymer, a rare earth metal ion doped polymer, a dye-doped silica, a rare-earth ion doped silica, and a rare earth ion doped alkaline earth metal fluoride nanoparticle; wherein the second fluorescence is generated by an entity selected from the group consisting of: a dye, a molecular probe, an indicator, a probe monomer, an indicator monomer, and a cross-linker; and wherein the first and second fluorescence differ at least by an emission wavelength and/or by an excitation wavelength.

To summarize, a double fluorescent particle comprising a core, the core having a first fluorescence; and a molecularly imprinted polymer (MIP) shell, the MIP having a second fluorescence is suggested, wherein the MIP is an organic polymer comprising elements selected from the group consisting of: C, H, O, N, P, and S; wherein the MIP is adapted to selectively bind to a cell surface structure; wherein the first fluorescence is generated by an entity, selected from a group encompassing: a carbon nanodot, a dye-doped polymer, a dye-doped stabilized micelle, a quantum dot doped polymer, a rare earth metal ion doped polymer, a dye-doped silica, a rare-earth ion doped silica, and a rare earth ion doped alkaline earth metal fluoride nanoparticle; wherein the second fluorescence is generated by an entity selected from the group consisting of: a dye, a molecular probe, an indicator, a probe monomer, an indicator monomer, and a cross-linker; and wherein the first and second fluorescence differ at least by an emission wavelength and/or by an excitation wavelength. Further, a method of screening for a target cell in a sample is suggested, the target cell being characterized by a cell surface structure which is recognized by the MIP, the method comprising: providing a double fluorescent particle as described; allowing a contact between the double fluorescent particle and a plurality of cells from the sample, the sample potentially comprising a cell having the cell surface structure; detecting a cell having the cell surface structure with bound thereto double fluorescing particles; and determining a presence of the target cell in the sample. Further, a method for establishing a target cell line is suggested, wherein the cells of the target cell line are characterized by a cell surface structure, the method comprising: isolating from a multitude of cells the target cell specified by the suggested screening method, and cultivating the isolated cell. Further, the use of the suggested double fluorescent particle for in vitro identification and/or characterization of circulating tumor cells in a blood sample is suggested. Further, the use of the suggested double fluorescent particle for identifying a cell, a cell line, or a hybridoma which produces a specific immunoglobulin or a specific cytokine is suggested. Further, an imaging technique for cancer detection in a tissue is suggested comprising: detecting a fluorescence ratio at a double fluorescent particle and generating an image of the tissue, wherein cells with a surface structure recognized by double fluorescing particles as suggested are highlighted against a background of the image. Furthermore, a cell sorting technique is suggested which comprises: labelling a cell with the suggested double fluorescent particle, detecting a ratio of first and second fluorescence signals; and registering the presence of a cell which is labelled by the double fluorescent particle.

The present invention has been explained with reference to various illustrative embodiments and examples. These embodiments and examples are not intended to restrict the scope of the invention, which is defined by the claims and their equivalents. As is apparent to one skilled in the art, the embodiments described herein can be implemented in various ways without departing from the scope of what is invented. Various features, aspects, and functions described in the embodiments can be combined with other embodiments.

REFERENCES

Ag, D.; Bongartz, R.; Dogan L. E.; Seleci, M.; Walter, Johanna-G.; Demirkol, D. O.; Stahl, F.; Ozcelik, S.; Timur, S.; Scheper, T. (2014) Biofunctional quantum dots as fluorescence probe for cell-specific targeting. Colloids and Surfaces B: Biointerfaces 114: 96-103

Amjadi, M. and Jalili, R. (2017) Molecularly imprinted mesoporous silica embedded with carbon dots and semiconductor quantum dots as a ratiometric fluorescent sensor for diniconazole. Biosensors and Bioelectronics 96: 121-126

Amjadi and Jalili (2018) A molecularly imprinted dual-emission carbon dot-quantum dot mesoporous hybrid for ratiometric determination of anti-inflammatory drug celecoxib. Spectrochimica Acta Part A: Molecular and Biomolecular Spectroscopy, 191: 345-351

Demir, B.; Lemberger, M. M.; Panagiotopoulou, M.; Rangel, P. X. M.; Timur, S.; Hirsch, T.; Bui, B. T. S.; Wegener, J.; Haupt, K. (2018) Tracking hyaluronan: molecularly imprinted polymer coated carbon dots for cancer cell targeting and imaging. ACS Applied Materials and Interfaces, 10: 3305-3313

Holzapfel, V.; Musyanovych, A.; Landfester, K.; Lorenz, M. R.; Mailänder, V. (2005) Preparation of fluorescent carboxyl and amino functionalized polystyrene particles by miniemulsion polymerization as markers for cells. Macromolecular Chemistry and Physics 206: 2440-2449

Jones, E. R., Semsarilar, M., Blanazs, A., and Armes, S. P. (2012). Efficient Synthesis of Amine-Functional Diblock Copolymer Nanoparticles via RAFT Dispersion Polymerization of Benzyl Methacrylate in Alcoholic Media. Macromolecules 45: 5091-5098

Long, Y.; Zhang, Z.; Yan, X.; Xing, J.; Zhang, K.; Huang, J.; Zheng, J.; Li, W. (2010) Multiplex immunodetection of tumor markers with a suspension array built upon core-shell structured functional fluorescence-encoded microspheres. Analytica Chimica Acta 665: 63-68

Mao, Y.; Bao, Y.; Han, D.; Li, F.; Niu, L. (2012) Efficient one-pot synthesis of molecularly imprinted silica nanospheres embedded carbon dots for fluorescent dopamine optosensing. Biosensors and Bioelectronics 38: 55-60

Ritter, B., Haida, P., Fink, F., Krahl, T., Gawlitza, K., Rurack, K., Scholz, G., Kemnitz, E. (2017). Novel and easy access to highly luminescent Eu and Tb doped ultra-small $CaF_2$, $SrF_2$ and $BaF_2$ nanoparticles—structure and luminescence. Dalton Transactions 46: 2925-2936

Stsiapura, V.; Sukhanova, A.; Artemyev, M.; Pluot, M.; Cohen, J. H. M.; Baranov, A. V.; Oleinikov, V.; Nabiev, I. (2004) Functionalized nanocrystal-tagged fluorescent polymer beads: synthesis, physicochemical characterization, and immunolabeling application. Analytical Biochemistry 334: 257-265

ABBREVIATIONS

ABDV=2,2'-azobis(2,4-dimethylvaleronitrile)
AFM=atomic force microscopy
AIBA=2,2'-azobis(2-methylpropionamidine)dihydrochloride
APS=ammoniumpersulfate
APTES=3-(aminopropyl)triethoxysilane
ATRP=atom transfer radical polymerization
BHT=butylhydroxytoluene
CND=carbon nanodot
CPBA=4-cyano-4-(phenylcarbonothioylthio)pentanoic acid DMF=dimethylformamide
EDX=energy dispersive x-ray diffraction
EGDMA=ethyleneglycol dimethacrylate
MeOH=CH$_3$OH, methanol
MeCN=CH$_3$CN, acetonitrile
MIP=molecularly imprinted polymer
MIS=molecularly imprinted silica
NBD-Cl=4-chloro-7-nitrobenzo[c][1,2,5]oxadiazole
NIP=non imprinted polymer (shell on particles for background signal control)
PS=polystyrene
QD=quantum dot
RAFT=reversible addition-fragmentation chain transfer
SA=N-acetylneuraminic acid=sialic acid
TBA-OH=tetrabutylammonium hydroxide
TEM=transmission electron microscopy
TEOS=tetraethylorthosilicate
TEMOS=tetramethylorthosilicate
THF=tetrahydrofuran
I=fluorescent dye according to formula (scheme 1):

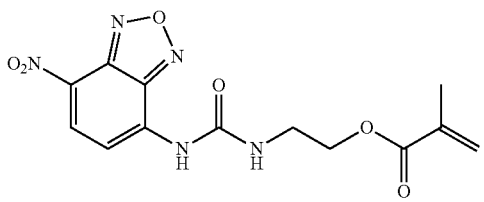

II=fluorescent dye according to formula (scheme 2):

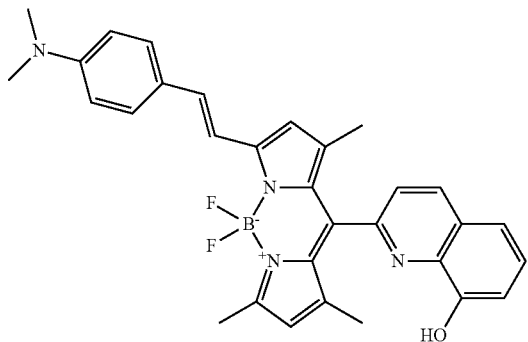 [SMILES: CC1=CC(C)=[N+]2C1=C(c1ccc3cccc(O)c3n1)c1c(C)cc(/C=C/c3ccc(N(C)C)cc3)n1[B-]2(F)F]

III=fluorescent dye according to formula (scheme 3):

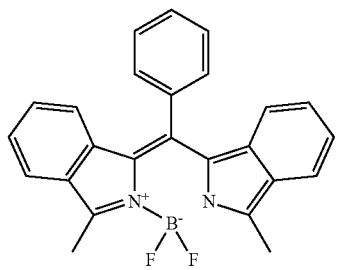

The invention claimed is:

1. A double fluorescent particle comprising:
a core, having a first fluorescence; and
a molecularly imprinted polymer shell having a second fluorescence, wherein the molecularly imprinted polymer is an organic polymer comprising elements selected from the group consisting of: C, H, O, N, P, and S; and
wherein the molecularly imprinted polymer is adapted to selectively bind to a cell surface structure;
wherein the first fluorescence is generated by an entity, selected from the group consisting of: a carbon nanodot, a dye-doped polymer, a dye-doped stabilized micelle, P-dot consisting essentially of a π-conjugated polymer, a quantum dot doped polymer, a rare earth metal ion doped polymer, a dye-doped silica, a rare-earth ion doped silica, and a rare earth ion doped alkaline earth metal fluoride nanoparticle;
wherein the second fluorescence is generated by an entity selected from the group consisting of: a dye, a molecular probe, an indicator, a probe monomer, an indicator monomer, and a cross-linker; and
wherein the first and second fluorescence differ at least by an emission wavelength and/or by an excitation wavelength.

2. The double fluorescent particle according to claim 1, further comprising:
a structural shell comprising SiO$_2$ or TiO$_2$ which covers the core, wherein the molecularly imprinted polymer shell is disposed atop the structural shell.

3. The double fluorescent particle according to claim 1, wherein a median arithmetic diameter of the particle as measured with an electron microscope lies in a range selected from 20 nm to less than 100 nm.

4. The double fluorescent particle according to claim 1, wherein a thickness of the molecularly imprinted polymer shell is selected from 2 nm to 25 nm.

5. The double fluorescent particle according to claim 1, wherein the MIP is adapted to bind to a cell surface structure selected from a glycan selected from Siaα2-6GalNAc (Sialyl Tn), Siaα2-3Galβ 1-3GalNAc (Sialyl T), Siaα 2,3 Galβ 1,4(Fucα 1,3)GlcNAc (Sialyl Lewis$^X$), Sia2,3Galβ 1,3(Fucα 1,4) GlcNAc (Sialyl Lewis$^A$), Siaα2,3-Galβ, Siaα 2,6-Galβ, Siaα2,3-N-acetyllactosamine, Siaα2,6-N-acetyllactosamine, N-acetylneuraminic acid (Neu5Ac, human form of sialic acid (SA)), N-glycolylneuraminic acid (Neu5Gc, animal form of sialic acid), GlcA2SO$_3$ 1,4-Glc2NSO$_3$ or GlcA2SO$_3$ 1,4-Glc2NSO$_3$6SO$_3$.

6. The double fluorescent particle according to claim 1, wherein the molecularly imprinted polymer is generated by a polymerization of at least one type of a monomer selected from: acrylamide, vinyl pyridine, N-isopropylacrylamide, 2-hydroxyethyl methacrylate, methyl methacrylate, benzyl methacrylate, methacrylate, methacrylamide, N,N'-dimethyl methacrylamide, trifluoromethyl acrylate, 2-aminoethyl methacrylate, vinylalcohol, vinylimidazole, vinylphenyl boronic acid, amino-substituted vinylphenyl boronic acid, vinyl benzaldehyde, vinyl aniline; with a crosslinking agent selected from: ethylene dimethacrylate, ethylene glycol dimethacrylate, N,N'-methylenediacrylamide, divinylbenzene, tetramethylene dimethacrylate, poly(acrylic acid), a bis(-hydroxyethyl) sulfone, trimethylolpropane trimethacrylate, and pentaerythritol triacrylate.

7. The double fluorescent particle claim 1, wherein the rare earth metal ion is selected from: cerium (Ce), europium (Eu), gadolinium (Gd), neodymium (Nd), scandium (Sc), terbium (Tb), ytterbium (Yb), yttrium (Y), dysprosium (Dy), samarium (Sm), holmium (Ho), erbium (Er), thulium (Tm), and praseodymium (Pr).

8. The double fluorescent particle according to claim 1, wherein the rare earth ion doped alkaline earth metal fluoride nanoparticle comprises a fluoride of Ca, Ba, or Sr; and the rare earth ion is selected from: Ce, Eu and Tb.

9. The double fluorescent particle according to claim 1, wherein the rare earth ion of the rare-earth ion doped silica is selected from: Terbium and Europium.

10. A method of screening for a target cell in a sample, the target cell being characterized by a cell surface structure, the method comprising:
providing a double fluorescent particle according to claim 1;
allowing a contact between the double fluorescent particle and a plurality of cells from the sample, potentially comprising a cell having the cell surface structure;
detecting a cell having the cell surface structure with bound thereto double fluorescent particles; and
determining a presence of the target cell in the sample.

11. The screening method according to claim 10, wherein detecting the cell comprises measuring a ratio of a first fluorescence and a second fluorescence of the double fluorescent particle.

12. The screening method according to claim 10, wherein the cell surface structure is a glycosylated protein or a glycosylated lipid.

13. The screening method according to claim 10, further comprising:
isolating the target cell.

14. A cell sorting technique comprising: labelling a cell with the double fluorescent particle according to claim 1, detecting a ratio of first and second fluorescence signals; and registering the presence of a cell which is labelled by the double fluorescent particle.

15. The cell sorting technique according to claim 14, wherein the molecularly imprinted polymer of the polymer shell of the double fluorescent particle is adapted to recognize a cell surface structure.

* * * * *